(12) United States Patent
Beccari et al.

(10) Patent No.: US 9,409,876 B2
(45) Date of Patent: Aug. 9, 2016

(54) BRADYKININ RECEPTOR ANTAGONISTS AND PHARMACEUTICAL COMPOSITIONS CONTAINING THEM

(71) Applicant: DOMPE' FARMACEUTICI S.P.A., Milan (IT)

(72) Inventors: Andrea Rosario Beccari, L'Aquila (IT); Gianluca Bianchini, L'Aquila (IT); Chiara Liberati, L'Aquila (IT); Michela Fani', L'Aquila (IT); Mara Zippoli, L'Aquila (IT)

(73) Assignee: DOMPE' FARMACEUTICI S.P.A., Milan (IT)

( * ) Notice: Subject to any disclaimer, the term of this patent is extended or adjusted under 35 U.S.C. 154(b) by 0 days.

(21) Appl. No.: 14/304,577

(22) Filed: Jun. 13, 2014

(65) Prior Publication Data

US 2014/0371274 A1    Dec. 18, 2014

(30) Foreign Application Priority Data

Jun. 14, 2013   (EP) .................................... 13172137

(51) Int. Cl.
| | |
|---|---|
| C07D 249/18 | (2006.01) |
| C07D 307/14 | (2006.01) |
| C07D 405/12 | (2006.01) |
| C07D 407/12 | (2006.01) |
| C07D 409/12 | (2006.01) |
| C07D 413/12 | (2006.01) |

(52) U.S. Cl.
CPC ............ C07D 307/14 (2013.01); C07D 405/12 (2013.01); C07D 407/12 (2013.01); C07D 409/12 (2013.01); C07D 413/12 (2013.01)

(58) Field of Classification Search
CPC .................................................. C07D 249/18
See application file for complete search history.

(56) References Cited

U.S. PATENT DOCUMENTS

| | | |
|---|---|---|
| 2004/0029920 A1 | 2/2004 | Kuduk et al. |
| 2004/0034064 A1 | 2/2004 | Kuduk et al. |
| 2004/0063761 A1 | 4/2004 | Kuduk et al. |
| 2006/0084699 A1 | 4/2006 | Barth et al. |
| 2006/0173023 A1 | 8/2006 | Wood et al. |
| 2006/0293332 A1 | 12/2006 | Grant et al. |

FOREIGN PATENT DOCUMENTS

| | | |
|---|---|---|
| FR | 2 840 897 | 12/2003 |
| WO | 96/06082 A1 | 2/1996 |
| WO | WO 97/25315 | 7/1997 |
| WO | WO 01/05783 | 1/2001 |
| WO | WO 02/092556 | 11/2002 |
| WO | 02/099388 A2 | 12/2002 |
| WO | 03/007958 A1 | 1/2003 |
| WO | 2004/054584 A1 | 7/2004 |
| WO | 2010/031577 A1 | 3/2010 |

OTHER PUBLICATIONS

European Search Report for EP Application No. 13 17 2137 mailed Sep. 19, 2013 (9 pages).
Database Registry—Chemical Abstracts Services—XP002712701—Database accession No. 1032894-83-9 "Compounds with CAS Registry No. 1032894-83-9, 1032894-63-5, 1032899-12-9, 1032899-03-8, 1032898-81-9, 1032895-16-1, 1032895-07-0." Jul. 7, 2008.
Database Registry—Chemical Abstracts Services—XP002712702—Database accession No. 1032751-65-7 "Compounds with CAS Registry No. 1032751-65-7, 1032751-71-5, 1032751-72-6." Jul. 4, 2008.
Austin et al., "Stable Expression of the Human Kinin B1 Receptor in Chinese Hamster Ovary Cells," The Journal of Biological Chemistry, 272(17):11420-11425 (1997).
Bennett et al., "A peripheral mononeuropathy in rat that produces disorders of pain sensation like those seen in man," Pain, 33:87-107 (1988).
Berge et al., "Pharmaceutical salts," Journal of Pharmaceutical Sciences, 66(1):1-19 (Jan. 1977).
Bock et al., "Bradykinin antagonists: new opportunities," Current Opinion in Chem. Biol., 4:401-406 (2000).
Chaplan et al., "Quantitative assessment of tactile allodynia in the rat paw," Journal of Neuroscience Methods, 53:55-63 (1994).
Heitsch, "The therapeutic potential of bradykinin B2 receptor agonists in the treatment of cardiovascular disease," Expert Opin. Investig. Drugs, 12:759-770 (2003).
Hess et al., "Cloning and Pharmacological Characterization of a Human Bradykinin (BK-2) Receptor" Biochem. Biophys. Res. Commun., 184:260-268 (1992).

(Continued)

Primary Examiner — Michael Barker
Assistant Examiner — Karen Cheng
(74) Attorney, Agent, or Firm — Ascenda Law Group, PC

(57) ABSTRACT

The present invention relates to compounds represented by formula (I)

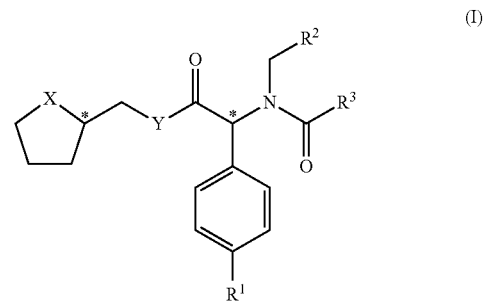

and pharmaceutically acceptable salts thereof that are antagonists of the bradykinin B1 receptor. These compounds are useful for the treatment of disorders associated with the bradykinin B1 pathway, in particular pain-related disorders.

22 Claims, 2 Drawing Sheets

(56) References Cited

OTHER PUBLICATIONS

Huang et al., "Increased Inositol 1, 4, 5-Trisphosphate Accumulation Correlates with an Up-Regulation of Bradykinin Receptors in Alzheimer's Disease," Journal of Neurochemistry, 64:761-766 (1995).

Leeb-Lundberg et al., "International Union of Pharmacology. XLV. Classification of the Kinin Receptor Family: from Molecular Mechanisms to Pathophysiological Consequences," Pharmacological Reviews, 57(1):27-77 (2005).

Marceau et al., "The B1 Receptors for Kinins," Pharmacological Reviews, 50(3):357-386 (1998).

Marceau et al., "Bradykinin Receptor Ligands: Therapeutic Perspectives," Nature Reviews Drug Discovery, 3:845-852 (Oct. 2004).

Marceau, "A possible common pharmacophore in the non-peptide antagonists of the bradykinin B1 receptor," Trends in Pharmacological Sciences, 26(3):116-118 (Mar. 2005).

Stewart, "Bradykinin Antagonists as Anti-Cancer Agents," Current Pharmaceutical Design, 9:2036-2042 (2003).

BRADYKININ RECEPTOR ANTAGONISTS AND PHARMACEUTICAL COMPOSITIONS CONTAINING THEM

This application claims benefit of Serial No. 13172137.5, filed 14 Jun. 2013 in the European Patent Office and which application is incorporated herein by reference.

BRIEF DESCRIPTION OF THE INVENTION

The present invention relates to compounds useful in the prevention or treatment of symptoms and disorders associated with the bradykinin $B_1$ pathway and to pharmaceutical compositions containing such compounds.

BACKGROUND OF THE INVENTION

The nonapeptide bradykinin (BK) and the physiologically-related decapeptide kallidin (KD) are endogenous vasoactive peptides generated as short-lived components of the kallikrein-kinin system. They play a key role in the regulation of normal physiological processes in the peripheral (PNS) and central (CNS) nervous systems and are effectors of a number of inflammatory responses, including bronchoconstriction, plasma extravasation, release of prostaglandins and leukotrienes, smooth muscle contraction and relaxation and nociception [Austin C. E. et al., *J. Biol. Chem.* (1997) 272, 11420-11425; Hess J. F. et al. *Biochem. Biophys. Res. Commun.* (1992) 184, 260-268]. Under pathophysiological conditions, elevated levels of kinins are rapidly produced from the circulating precursors kininogens by enzymatic action of trypsine-like serine proteases, kallikrein and tissue kallikrein.

Kinins exert their action interacting with two cell surface receptors, Bradykinin B1 receptor (BKB1R) and Bradykinin B2 receptor (BKB2R), belonging to the 7TM-GPCR superfamily.

BKB2Rs are constitutively expressed in most cells and tissue types and mediate the most of acute effects due to BK and KD after their production in plasma and tissues, respectively. BKB1Rs are poorly constitutively expressed under physiological conditions and are induced following inflammatory insults or noxious stimuli, although recent data show the presence of constitutive BKB1Rs in rat and mouse CNS, making BKB1R a particularly attractive drug target.

Overproduction of kinins under pathophysiological conditions is implicated in the pathogenesis of a number of clinically-relevant disorders, including pain, inflammation, hypotension, asthma, colitis, rhinitis, pancreatitis, sepsis and rheumatoid arthritis [Leeb-Lundberg L. M. F. et al., *Pharmacol. Rev.* (2005) 57, 57, 27-77]. BK is also implicated in peripheral inflammatory processes associated with Alzheimer's disease [Huang H. M. et al., *J. Neurochem.* (1995) 64, 761-766] and Yong Y. I et al in the growth of several solid tumors [Stewart J. M. *Curr. Pharm. Design* (2003) 9, 2036-2042]. The role of kinins, specifically BK, in pain and inflammation has been well documented [Marceau F. et al. *Nat. Rev. Drug Discov.* (2004) 3, 845-852] and has provided impetus to the development of potent and selective BK antagonists. BKB1R is an attractive target to treat inflammation, because it is absent in normal tissues in most systems, but it is inducible following tissue injury under the control of inflammatory cytokines, mitogen-activated protein kinase (MAPK) pathways and some transcription factors such as nuclear factor B (NF-B). BKB1R is more resistant than BKB2R to desensitization [Marceau F. et al. *Pharmacol. Rev.* (1998) 50, 357-386] making BKB1R antagonism more adapted to chronic or persistent inflammatory systems than BKB2R antagonism.

Moreover, kinins have been demonstrated to exert a cardio-protective role which is mediated by BKB2Rs [Heitsch H. *Expert Opin. Investig. Drugs* (2003) 12, 759-770] as evidenced by BKB2R agonists in alleviating congestive heart failure, hypertension and ischemic heart disease which raises concerns on the clinical use of BKB2R antagonists.

On this basis, several research programs have been initiated for the identification of novel non-peptide ligands binding BKB1 receptors replacing classical peptide antagonists. In recent years these efforts have been heightened with the expectation that useful therapeutic agents with anti-inflammatory properties would provide relief from diseases mediated by a BK receptor pathway [Bock M. G. et al. *Current Opinion in Chem. Biol.* (2000) 4, 401-406]. The non-peptide BKB1R antagonists that have appeared in the literature since the year 2000 and several of the disclosed structures, generated by different laboratories and belonging to different chemical classes, all share the pharmacophore group "RN—$SO_2$-phenyl" [Marceau F. *TRENDS Pharmacol. Sc.* (2005) 26, 116-118] that has allowed to derive a hypothesis of docking to the human BKB1 receptor and suggests structural commonalities and a preferential molecular mode of action within the selected compounds.

In the last few years, several classes of non-peptide BKB1R antagonists have been disclosed. Three main classes have been claimed by several pharmaceutical companies:
1) N-(Arylsulfonyl)aminoacid derivatives [Sanofi WO9725315 (1997); Novartis WO 00075107 (2000) and WO02092556 (2002); Bayer AG WO03007958 (20039; Elan Pharmaceuticals WO03093245 (2003); Lab. Fournier SA FR2840897 (2003); Merck & Co. INC. WO2004/054584 (2004)];
2) Biaryl derivatives [Pharmacopeia Inc. WO0105783 (2001); Merck & Co. INC. US2004034064 (2004), US2004029920 (2004), US 2004063761 (2004)];
3) Benzodiazepine derivatives [Merck & Co. INC. WO02099388 (2002)].
4) Dihydropyridine derivatives as Bradykinin Antagonists [Pfizer Inc. WO96/06082].
5) Sulfonylquinoxalone derivatives [US 2006/0293332].

Nevertheless, it is necessary to find new classes of bradykinin receptor B1 antagonist, because of their high therapeutic potential.

The present inventors have identified a novel class of compounds acting as selective BKB1R antagonists.

SUMMARY OF THE INVENTION

The present inventors have now found a novel class of compounds having activity as selective bradykinin B1 receptor antagonists. Said compounds are useful in the treatment of pathologies dependent on the bradykinin B1 receptor pathways.

DETAILED DESCRIPTION OF THE INVENTION

Figure 1:
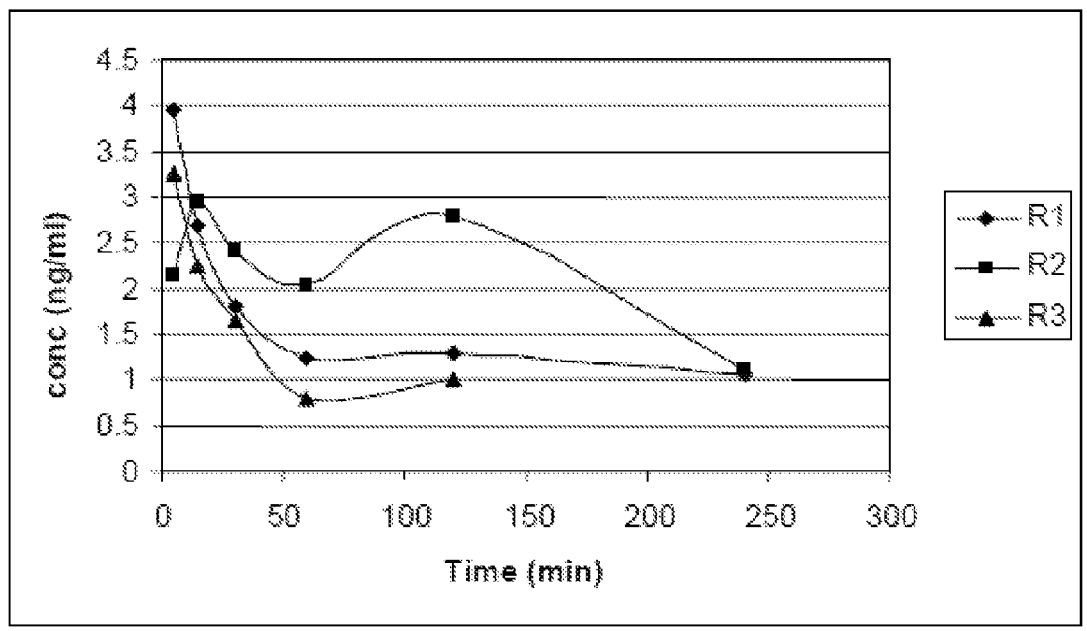
FIG. 1 shows the plasma concentrations, expressed in ng/ml, of 3-methyl-N-(2-methoxybenzyl)-N-{[(1R)-1-(4-methylphenyl)]-2-oxo-2-[(2R)-(tetrahydrofuran-2-ylmethyl)amino]ethyl}butanamide (compound 8 (R,R)), over time after oral administration for each of the three subjects tested (R1, R2 and R3).

The present invention provides compounds of formula (I):

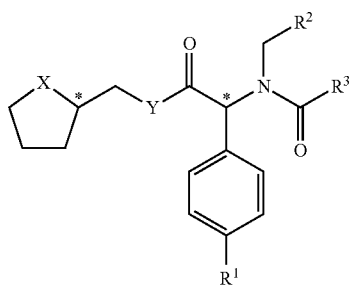

(I)

and pharmaceutically acceptable salts thereof, wherein
X and Y are different one from the other and are O or NH;
$R^1$ is selected from the group consisting of
$C_1$-$C_6$-alkyl, preferably $C_1$-$C_3$ alkyl, more preferably methyl;
$C_3$-$C_6$-cycloalkyl, preferably cyclopropyl;
and halo $C_1$-$C_3$-alkyl.

Preferably, said halo $C_1$-$C_3$ alkyl is a methyl substituted with at least one halogen atom, preferably selected from Cl and F. More preferably said halo $C_1$-$C_3$ alkyl is selected from fluoro-methyl; difluoro-methyl and trifluoro-methyl. Particularly preferred identity of said halo $C_1$-$C_3$-alkyl is trifluoromethyl.

$R^2$ is selected from the group consisting of:
$C_1$-$C_8$ alkyl, preferably $C_3$-$C_5$ alkyl;
$C_3$-$C_6$ cycloalkyl, preferably selected from $C_5$ or $C_6$ cycloalkyl; preferably said $C_3$-$C_6$ cycloalkyl is unsubstituted;
phenyl unsubstituted or substituted with at least one group selected from a —O—$C_1$-$C_4$-akyl, preferably methoxy, and $C_1$-$C_4$-alkyl, preferably methyl; more preferably when said phenyl is substituted by a —O—$C_1$-$C_4$-akyl, the latter group is in position ortho of the phenyl ring.
benzothiophene, preferably benzothiophen-3-yl; and
a 5 or 6 membered-heteroaromatic ring.

Preferably, said 5 or 6 membered heteroaromatic ring is selected from the group consisting of pyridine and pyrrole. More preferably, said 5 or 6 membered heteroaromatic ring is selected in the group consisting of N-methyl pyrrole, preferably N-methyl-pyrrol-2-yl, and pyridin-3-yl.

$R^3$ is selected from the group consisting of:
$C_1$-$C_8$ alkyl, preferably $C_2$-$C_4$ alkyl;
$(CH_2)_m COCH_3$, wherein m is an integer comprised between 1 and 4, preferably 2.
$(CH_2)_n$—Z, wherein n is an integer comprised between 1 and 3, preferably 1 and Z is selected from the group consisting of dialkylamine, preferably di-$C_1$-$C_3$-alkylamine, more preferably dimethylamine; $C_3$-$C_6$-cycloalkyl among which $C_5$-cycloalkyl is particularly preferred; benzotriazole, preferably benzotriazol-1-yl; isoindol-1,3(2H)-dione-2-yl; imidazole, preferably imidazol-4-yl; triazole, preferably 1,2,3-triazol-1-yl; indole, preferably indol-1-yl; furane, preferably furan-2-yl; and phenyl, the latter being unsubstituted or substituted with one or more groups selected from halo, preferably F, or $C_1$-$C_3$ alkyl, preferably methyl, O—$C_1$-$C_3$ alkyl, preferably methoxy, more preferably methoxy in position 2 of the phenyl ring, and $C_1$-$C_3$ alkylamino, preferably dimethylamino;
$C_3$-$C_6$ cycloalkyl unsubstituted or substituted with one or more groups selected from halo, preferably F, and $C_1$-$C_3$ alkyl, preferably methyl;
2-methyl-1,3-oxazol-4-yl;
phenyl unsubstituted or substituted with one or more groups selected from $C_1$-$C_3$ alkyl, preferably methyl; hydroxyl; halo, preferably F; and nitro.

As utilized herein, the term "alkyl", alone or in combination, means a straight or branched-chain alkyl radical or group. Preferred branched alkyls according to the present invention are isopropyl, isobutyl or tert-butyl.

The phrase "pharmaceutically acceptable salt(s)", as used herein, means those salts of compounds of the invention that are safe and effective for systemic use in mammals and that possess the desired biological activity. Pharmaceutically acceptable salts include salts of acidic or basic groups present in compounds of the invention. Certain compounds of the invention can form pharmaceutically acceptable salts with various amino acids. For a review on pharmaceutically acceptable salts see BERGE ET AL., 66 J. PHARM. SCI. 1-19 (1977).

It is particularly preferred, if the salt is a tartrate or hydrocloride or lysine salt.

According to a preferred embodiment of the invention X is O and Y is NH.

According to a particularly preferred embodiment of the invention, also in combination with the preceding embodiment, in said compounds of formula I, $R^1$ is selected from methyl, cyclopropyl and trifluoromethyl. Most preferred among these compounds are those wherein $R^1$ is methyl.

According to a further preferred embodiment of the invention, also in combination with any of the preceding embodiments, in the above compounds of formula I, $R^2$ is selected from $C_3$-$C_5$ alkyl; $C_5$ or $C_6$ cycloalkyl; phenyl unsubstituted or substituted with metoxy or methyl; benzothiophen-3-yl; N-methyl-pyrrol-2-yl and pyridine-3-yl. Particularly preferred among these are compounds wherein $R^2$ is selected from the group consisting of: methoxyphenyl, preferably 2-methoxyphenyl, methylphenyl, preferably 3-methylphenyl or 4 methylphenyl, 1-benzothiophen-3-yl, 1-ethylpropyl, 1-methyl-1H-pyrrol-2-yl, 2-methylethyl, pyridin-3yl, cyclopentyl and cyclohexyl. Mostly preferred among these compounds are those wherein $R^2$ is selected from 2-methoxyphenyl.

According to a further preferred embodiment of the invention, also in combination with any of the preceding embodiments, in the above compounds of formula I, $R^3$ is selected from: $C_2$-$C_4$ alkyl; 4yl-butan-2one; —$CH_2$—Z wherein Z is dimethylamino, cyclopentyl, benzotriazol-1-yl, isoindol-1,3 (2H)-dione-2-yl, imidazol-4-yl, 1,2,3-triazol-1-yl, indol-1-yl, furan-2-yl, or phenyl, unsubstituted or substituted with one or more groups selected from F, methyl, methoxy and dimethylamino; $C_3$-$C_6$ cycloalkyl unsubstituted or substituted with one or more groups selected from F and methyl; 2-methyl-1,3-oxazol-4-yl; phenyl unsubstituted or substituted with one or more groups selected from methyl, hydroxy, F and nitro; dimethylamino.

Particularly preferred among these compounds are compounds wherein $R^3$ is selected from 1-methylen-1H-benzotriazole; 2-methyl-1,3-oxazol-4-yl; 2-methylen-1H-isoindole-1,3(2H)-dione; N,N-dimethyl-1-methylenamine; 4-methylen-1H-imidazole; 4-yl-butan-2-one; 1-methylen- 1H-1,2,3-triazole; 1-methylen-1H-indole; benzyl; 2-methoxybenzyl; 2-methylbenzyl; 3-methylbenzyl; 4-methylbenzyl; 2,3-difluorobenzyl; 4-fluorobenzyl; 2,6-difluorobenzyl; 4-N,N-dimethylaminobenzyl; 4-methylphenyl; 4-hydroxyphenyl; 4-nitrophenyl; 2-nitrophenyl; 4-fluorophenyl; 2-methylenfurane; ethyl; butyl; isobutyl; phenyl; 4,4-difluorocyclohexyl; cyclohexyl; cyclopentyl; cyclobutyl; cyclopropyl; 1-yl-2-methylcyclopropane; methylencyclopentyl. Even more preferred among these compounds are those wherein $R^3$ is selected from 1-methylen-1-H-benzotriazole; 2-methyl-1,3-oxazol-4-yl; benzyl; 2,3-difluorobenzyl; 2,6-difluorobenzyl; 2-methylenfurane; 2-methylbenzyl; 2-methylen-1H-isoindole-1,3(2H)-dione; 4-methylen-1H-imidazole; 2-methoxybenzyl; butyl; isobutyl; cyclopentyl; 3-methylbenzyl; 1-methylen-1H-1,2,3-triazole; 1-methylen-1H-indole and N,N-dimethyl-1-methylenamine. Most preferred among these compounds are compounds wherein $R^3$ is selected from 1-methylen-1-H-benzotriazole; 2-methyl-1,3-oxazol-4-yl; 4-methylen-1H-imidazole; 1-methylen-1H-1,2,3-triazole; 1-methylen-1H-indole and isobutyl.

According to a particularly preferred embodiment of the invention, in the compounds of formula I:

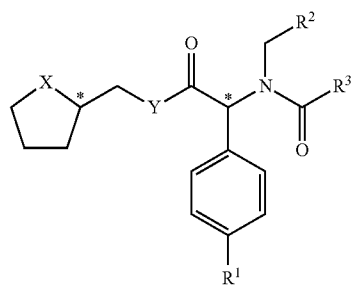

X is O;
Y is NH;
$R^1$ is selected from methyl, cyclopropyl and trifluoromethyl, preferably methyl;
$R^2$ is selected from methoxyphenyl, preferably 2-methoxyphenyl, methylphenyl, preferably 3-methylphenyl or 4 methylphenyl, 1-benzothiophen-3-yl, 1-ethylpropyl, 1-methyl-1H-pyrrol-2-yl, 2-methylethyl, pyridin-3yl, cyclopentyl and cyclohexyl.
$R^3$ is selected from 1-methylen-1H-benzotriazole; 2-methyl-1,3-oxazol-4-yl; 2-methylen-1H-isoindole-1,3(2H)-dione; N,N-dimethyl-1-methylenamine; 4-methylen-1H-imidazole; 4-yl-butan-2-one; 1-methylen-1H-1,2,3-triazole; 1-methylen-1H-indole; benzyl; 2-methoxybenzyl; 2-methylbenzyl; 3-methylbenzyl; 4-methylbenzyl; 2,3-difluorobenzyl; 4-fluorobenzyl; 2,6-difluorobenzyl; 4-N,N-dimethylaminobenzyl; 4-methylphenyl; 4-hydroxyphenyl; 4-nitrophenyl; 2-nitrophenyl; 4-fluorophenyl; 2-methylenfurane; ethyl; butyl; isobutyl; phenyl; 4,4-difluorocyclohexyl; cyclohexyl; cyclopentyl; cyclobutyl; cyclopropyl; 1-yl-2-methylcyclopropane; methylencyclopenty Particularly preferred compounds of formula I according to the invention, represented in Table I, are selected from:
2-(1H-benzotriazol-1-yl)-N-(2-methoxybenzyl)-N-{1-(4-methylphenyl)-2-oxo-2-[(tetrahydrofuran-2-ylmethyl)amino]ethyl}acetamide (compound number 1)
2-methyl-N-(2-methoxybenzyl)-N-{1-(4-methylphenyl)-2-oxo-2-[(tetrahydrofuran-2-ylmethyl)amino]ethyl}-1,3-oxazole-4-carboxamide (compound number 2)
2-(2,3-difluorophenyl)-N-(2-methoxybenzyl)-N-{1-(4-methylphenyl)-2-oxo-2-[(tetrahydrofuran-2-ylmethyl)amino]ethyl}acetamide (compound number 3)
N-(2-methoxybenzyl)-N-{1-(4-methylphenyl)-2-oxo-2-[(tetrahydrofuran-2-ylmethyl)amino]ethyl}furan-2-carboxamide (compound number 4)
2-(2,4-difluorophenyl)-N-(2-methoxybenzyl)-N-{1-(4-methylphenyl)-2-oxo-2-[(tetrahydrofuran-2-ylmethyl)amino]ethyl}acetamide (compound number 5)
2-(2,6-difluorophenyl)-N-(2-methoxybenzyl)-N-{1-(4-methylphenyl)-2-oxo-2-[(tetrahydrofuran-2-ylmethyl)amino]ethyl}acetamide (compound number 6)
N-(2-methoxybenzyl)-N-{1-(4-methylphenyl)-2-oxo-2-[(tetrahydrofuran-2-ylmethyl)amino]ethyl}-2-phenylacetamide (compound number 7)
3-methyl-N-(2-methoxybenzyl)-N-{(1-(4-methylphenyl)-2-oxo-2-[(tetrahydrofuran-2-ylmethyl)amino]ethyl}butanamide (compound number 8)
2-(methylphenyl)-N-(2-methoxybenzyl)-N-{(1-(4-methylphenyl)-2-oxo-2-[(tetrahydrofuran-2-ylmethyl)amino]ethyl}acetamide (compound number 9)
2-(1,3-dioxoisoindolin-2-yl)-N-(2-methoxybenzyl)-N-{1-(4-methylphenyl)-2-oxo-2-[(tetrahydrofuran-2-ylmethyl)amino]-ethyl}acetamide (compound number 10)
2-(dimethylamino)-N-(2-methoxybenzyl)-{1-(4-methylphenyl)-2-oxo-2-[(tetrahydrofuran-2-ylmethyl)amino]ethyl}acetamide (compound number 11)
2-(1H-imidazol-4-yl)-N-(2-methoxybenzyl)-N-{1-(4-methylphenyl)-2-oxo-2-[(tetrahydrofuran-2-ylmethyl)amino]ethyl}acetamide (compound number 12)
2-(2-methoxyphenyl)-N-(2-methoxybenzyl)-N-{(1-(4-methylphenyl)-2-oxo-2-[(tetrahydrofuran-2-ylmethyl)amino]ethyl}acetamide (compound number 13)
N-(2-methoxybenzyl)-N-{1-(4-methylphenyl)-2-oxo-2-[(tetrahydrofuran-2-ylmethyl)amino]ethyl}pentanamide (compound number 14)
N-(2-methoxybenzyl)-N-{1-(4-methylphenyl)-2-oxo-2-[(tetrahydrofuran-2-ylmethyl)amino]ethyl}cyclopentanecarboxamide (compound number 15)
4-hydroxy-N-(2-methoxybenzyl)-N-{1-(4-methylphenyl)-2-oxo-2-[(tetrahydrofuran-2-ylmethyl)amino]ethyl}benzamide (compound number 16)
4-oxo-N-(2-methoxybenzyl)-N-{1-(4-methylphenyl)-2-oxo-2-[(tetrahydrofuran-2-ylmethyl)amino]ethyl}pentanamide (compound number 17)
2-(3-methylphenyl)-N-(2-methoxybenzyl)-N-{(1-(4-methylphenyl)-2-oxo-2-[(tetrahydrofuran-2-ylmethyl)amino]ethyl}acetamide (compound number 18)
2-(4-methylphenyl)-N-(2-methoxybenzyl)-N-{(1-(4-methylphenyl)-2-oxo-2-[(tetrahydrofuran-2-ylmethyl)amino]ethyl}acetamide (compound number 19)
4-methyl-N-(2-methoxybenzyl)-N-{1-(4-methylphenyl)-2-oxo-2-[(tetrahydrofuran-2-ylmethyl)amino]ethyl}benzamide (compound number 20)
2-(4-fluorophenyl)-N-(2-methoxybenzyl)-N-{(1-(4-methylphenyl)-2-oxo-2-[(tetrahydrofuran-2-ylmethyl)amino]ethyl}acetamide (compound number 21)
4-fluoro-N-(2-methoxybenzyl)-N-{1-(4-methylphenyl)-2-oxo-2-[(tetrahydrofuran-2-ylmethyl)amino]ethyl}benzamide (compound number 22)
4,4-difluoro-N-(2-methoxybenzyl)-N-{1-(4-methylphenyl)-2-oxo-2-[(tetrahydrofuran-2-ylmethyl)amino]ethyl}cyclohexanecarboxamide (compound number 23)
N-(2-methoxybenzyl)-N-{1-(4-methylphenyl)-2-oxo-2-[(tetrahydrofuran-2-ylmethyl)amino]ethyl}propanamide (compound number 24)

N-(2-methoxybenzyl)-N-{1-(4-methylphenyl)-2-oxo-2-[(tetrahydrofuran-2-ylmethyl)amino]ethyl}cyclobutanecarboxamide (compound number 25)

N-(2-methoxybenzyl)-2-nitro-N-{1-(4-methylphenyl)-2-oxo-2-[(tetrahydrofuran-2-ylmethyl)amino]ethyl}benzamide (compound number 26)

N-(2-methoxybenzyl)-N-{1-(4-methylphenyl)-2-oxo-2-[(tetrahydrofuran-2-ylmethyl)amino]ethyl}cyclopropanecarboxamide (compound number 27)

N-(2-methoxybenzyl)-4-nitro-N-{1-(4-methylphenyl)-2-oxo-2-[(tetrahydrofuran-2-ylmethyl)amino]ethyl}benzamide (compound number 28)

2-[(4-dimethylamino)phenyl]-N-(2-methoxybenzyl)-N-{1-(4-methylphenyl)-2-oxo-2-[(tetrahydrofuran-2-ylmethyl)amino]ethyl}acetamide (compound number 29)

N-(2-methoxybenzyl)-N-{1-(4-methylphenyl)-2-oxo-2-[(tetrahydrofuran-2-ylmethyl)amino]ethyl}-2-(1H-1,2,3-triazol-1-yl)acetamide (compound number 30)

2-(1H-indol-1-yl)-N-(2-methoxybenzyl)-N-{1-(4-methylphenyl)-2-oxo-2-[(tetrahydrofuran-2-ylmethyl)amino]ethyl}acetamide (compound number 31)

N-(cyclopentylmethyl)-2-(1H-imidazol-4-yl)-N-{1-(4-methylphenyl)-2-oxo-2-[(tetrahydrofuran-2-ylmethyl)amino]ethyl}acetamide (compound number 32)

N-(cyclohexylmethyl)-2-(2-methylphenyl)-N-{1-(4-methylphenyl)-2-oxo-2-[(tetrahydrofuran-2-ylmethyl)amino]ethyl}acetamide (compound number 33)

N-(cyclohexylamino)-2-(dimethylamino)-N-{1-(4-methylphenyl)-2-oxo-2-[(tetrahydrofuran-2-ylmethyl)amino]ethyl}acetamide (compound number 34)

2-(dimethylamino)-N-(3-methylbenzyl)-N-{1-(4-methylphenyl)-2-oxo-2-[(tetrahydrofuran-2-ylmethyl)amino]ethyl}acetamide (compound number 35)

N-(cyclohexylmethyl)-2-(1H-imidazol-4-yl)-N-{1-(4-methylphenyl)-2-oxo-2-[(tetrahydrofuran-2-ylmethyl)amino]ethyl}acetamide (compound number 36)

N-(cyclohexylmethyl)-2-phenyl-N-{1-(4-methylphenyl)-2-oxo-2-[(tetrahydrofuran-2-ylmethyl)amino]ethyl}acetamide (compound number 37)

2-methyl-N-(3-methylbenzyl)-N-{1-(4-methylphenyl)-2-oxo-2-[(tetrahydrofuran-2-ylmethyl)amino]ethyl}cyclopropanecarboxamide (compound number 38)

N-(1-benzothiophen-3-ylmethyl)-2-(dimethylamino)-N-{1-(4-methylphenyl)-2-oxo-2-[(tetrahydrofuran-2-ylmethyl)amino]ethyl}acetamide (compound number 39)

N-(cyclohexylmethyl)-2-(3-methylphenyl)-N-{1-(4-methylphenyl)-2-oxo-2-[(tetrahydrofuran-2-ylmethyl)amino]ethyl}acetamide (compound number 40)

N-(2-ethylbutyl)-2-(2-methylphenyl)-N-{1-(4-methylphenyl)-2-oxo-2-[(tetrahydrofuran-2-ylmethyl)amino]ethyl}acetamide (compound number 41)

N-(2-ethylbutyl)-2-(4-fluorolphenyl)-N-{1-(4-methylphenyl)-2-oxo-2-[(tetrahydrofuran-2-ylmethyl)amino]ethyl}acetamide (compound number 42) 2-(dimethylamino)-N-[(1-methyl-1H-pyrrol-2-yl)methyl]-N-{1-(4-methylphenyl)-2-oxo-2-[(tetrahydrofuran-2-ylmethyl)amino]ethyl}acetamide (compound number 43)

N-(cyclopentylmethyl)-2-(2-methylphenyl)-N-{1-(4-methylphenyl)-2-oxo-2-[(tetrahydrofuran-2-ylmethyl)amino]ethyl}acetamide (compound number 44)

N-(cyclopentylmethyl)-2-(3-methylphenyl)-N-{1-(4-methylphenyl)-2-oxo-2-[(tetrahydrofuran-2-ylmethyl)amino]ethyl}acetamide (compound number 45)

2-(2-methylphenyl)-N-(pyridin-3-ylmethyl)-N-{1-(4-methylphenyl)-2-oxo-2-[(tetrahydrofuran-2-ylmethyl)amino]ethyl}acetamide (compound number 46)

N-(cyclopentylmethyl)-N-{1-(4-methylphenyl)-2-oxo-2-[(tetrahydrofuran-2-yl)methylamino]ethyl}2-phenylacetamide (compound number 47)

N-(cyclohexylmethyl)-2-cyclopentyl-N-{1-(4-methylphenyl)-2-oxo-2-[(tetrahydrofuran-2-ylmethyl)amino]ethyl}acetamide (compound number 48)

2-(1H-imidazol-4-yl)-N-(2-methylpropyl)-N-{1-(4-methylphenyl)-2-oxo-2-[(tetrahydrofuran-2-ylmethyl)amino]ethyl}acetamide (compound number 49)

N-(2-ethylbutyl)-N-{1-(4-methylphenyl)-2-oxo-2-[(tetrahydrofuran-2-ylmethyl)amino]ethyl}cyclohexanecarboxamide (compound number 50)

2-cyclopentyl-N-cyclopentylmethyl-N-{1-(4-methylphenyl)-2-oxo-2-[(tetrahydrofuran-2-ylmethyl)amino]ethyl}acetamide (compound number 51)

N-(2-methoxybenzyl]-N-[1-(4-cyclopropylphenyl)-2-oxo-2-[(tetrahydrofuran-2-yl)methylamino]ethyl)-3-methylbutanamide (compound number 52)

2-(1H-benzotriazol-1-yl)-N-(2-methoxybenzyl)-N-{1-(4-trifluoromethylphenyl)-2-oxo-2-[(tetrahydrofuran-2-ylmethyl)amino]ethyl}acetamide (compound number 53)

N-[(2-methoxybenzyl]-N-{1-[4-(trifluoromethyl)phenyl]-2-oxo-2-[(tetrahydrofuran-2-yl)methylamino]ethyl}3-methylbutanamide (compound number 54)

N-(2-methoxybenzyl)-N-{(1R)-1-(4-methylphenyl)-2-oxo-2-[(2R)-(pyrrolidin-2-ylmethyl)amino]ethyl}-2-(1H-1,2,3-triazol-1-yl)acetate (compound number 55)

Particularly preferred among the above compounds are compounds number 1, 2, 3, 4, 6, 7, 8, 9, 10, 12, 13, 14, 15, 18, 30, 31, 32, 34, 52, 53, 54 and 55.

The compounds of formula I according to the present invention comprise two chiral atoms, indicated in formula I with an asterix, that give origin to a number of steroisomers.

Thus, the compounds of the invention can be in different steric configurations such as R,S; S,S; S,R or R,S.

The present invention is directed to the above compounds as single stereoisomers or as mixtures thereof.

As will be shown in the experimental section, the present inventors have found that, surprisingly, the R,R configuration corresponds to a striking increase in the biological activity of the compounds of the invention.

Therefore, particularly preferred are the above said compounds of formula I wherein the two chiral atoms are both in R-configuration.

Mostly preferred among these compounds are those in which the two chiral atoms of formula I are in the R, R configuration.

The above listed compounds 1 to 55 are potent antagonists of the BKB1 receptor. As will be described in details in Example 56, all the compounds have been tested in a high-throughput screening (HTS) cellular-based assay for the human BKB1R and have shown an antagonist activity for this specific receptor at a concentration in the low micromolar range. Furthermore, all the compounds have been tested in a calcium mobilization assay and have shown activity as BKB1 receptor antagonists. Table II shows the different IC50-value obtained for most of the tested compounds.

Thus, a second object of the present invention are the above compounds of formula (I) for use as antagonists of BKB1 receptor, preferably of human BKB1 receptor.

This activity has also been confirmed in in vivo experiments carried out on representative compound 3-methyl-N-(2-methoxybenzyl)-N-{[(1R)-1-(4-methylphenyl)]-2-oxo-2-[(2R)-(tetrahydrofuran-2-ylmethyl)amino]ethyl}butanamide (compound 8 (R,R)), as described in Example 57.

In details, the evaluation of the in vivo activity of the compound was performed by testing the inhibition potential of compound 8 (R,R) in case of mechanical allodynia using the chronic constriction model of pain. The compound showed strong inhibitory activity on allodynia.

Furthermore, as shown in Example 58 the compounds of formula I according to the invention have an optimal pharmacokinetic profile.

Thus, the compounds of the invention are particularly suitable to be used in therapy.

Accordingly, a third object of the present invention are the above compounds for use as medicaments.

A fourth object of the present invention are the above compounds for use in the prevention, reduction of the risk of, amelioration and/or treatment of diseases associated with the activity of BKB1 receptor.

As has already been discussed in the background of the invention, BKB1 receptor is responsible for the pathogenesis of disorders involving pain and inflammation.

Preferably, said diseases associated with the activity of BKB1 receptor are selected from pain related disease, preferably selected from the group consisting of visceral pain; neuropathic pain, preferably post herpetic neuralgia or nerve injury; central pain syndromes caused by a lesion of the nervous system; postsurgical pain syndromes; bone and joint pain, repetitive motion pain; dental pain; cancer pain; myofascial pain; fibromyalgia; perioperative pain; chronic pain; dysmenorrea; pain associated with angina and inflammatory pain According to a preferred embodiment of the invention said visceral pain is pain associated with pancreatitis, cystitis or renal colic.

According to a further preferred embodiment of the invention, also in combination with the preceding embodiments, said neuropathic pain is neuropathic pain is post herpetic neuralgia or nerve injury.

According to a further preferred embodiment of the invention, also in combination with the preceding embodiments, said myofascial pain is muscular injury.

According to a further preferred embodiment of the invention, also in combination with the preceding embodiments, said inflammatory pain is pain associated with osteoarthritis, rheumatoid arthritis, rheumatic disease, gout, hyper-reactive airways, airways disease, among which particularly preferred are asthma, allergic asthma, bronchoconstriction, occupational asthma, viral or bacterial-exacerbation of asthma, other non-allergic asthmas, "wheezy-infant syndrome", chronic obstructive pulmonary disease. Preferably, said chronic obstructive pulmonary disease comprises emphysema, ARDS, bronchitis, pneumonia, pneumoconiosis, allergic and vasomotor rhinitis. Preferably, said pneumoconiosis comprises aluminosis, anthracosis, asbestosis, chalicosis, ptilosis, siderosis, tabacosis and byssinosis.

In an alternative preferred embodiment of the invention said disease associated with the activity of BKB1 receptor is an inflammatory and/or neuropathic condition, preferably selected from inflammatory bowel diseases; inflammatory skin disorders; edema resulting from burns, sprains and fractures; cerebral edema and angioedema; diabetic vasculopathy; diabetic neuropathy; diabetic retinopathy; diabetic symptoms associated with insulitis; liver disease; multiple sclerosis; cardiovascular disease; congestive heart failure; myocardial infarct; neurodegenerative diseases; epilepsy; septic shock; headache including cluster headache, migraine including prophylactic and acute use; closed head trauma; cancer; sepsis; gingivitis; osteoporosis; benign hyperplasia and hyperactive bladder.

According to a preferred embodiment of the invention said, inflammatory bowel diseases are Crohn's disease and ulcerative colitis or uveitis.

According to a further preferred embodiment of the invention, also in combination with the preceding embodiments, said inflammatory skin disorders are psoriasis and eczema.

According to a further preferred embodiment of the invention, also in combination with the preceding embodiments, said cardiovascular disease is atherosclerosis.

According to a further preferred embodiment of the invention, also in combination with the preceding embodiments, said neurodegenerative diseases are Parkinson's and Alzheimer's disease.

It is most preferably that the compounds of formula I are used for the prevention, reduction of the risk of, amelioration and/or treatment of inflammatory bowel disease and atherosclerosis.

It is further most preferably that the compound is used for the prevention, reduction of the risk of, amelioration and/or treatment of diabetic neuropathy and Alzheimer's disease.

A fourth object of the invention is a pharmaceutical composition comprising as the active ingredient at least one compound of formula I of the invention in combination with suitable pharmaceutically acceptable excipients and/or diluents. According to a preferred embodiment said pharmaceutical composition is for the prevention, reduction of the risk of, amelioration and/or treatment of a disease associated with activity of BKB1 receptor, as defined above. According to an embodiment, said pharmaceutical composition contains at least one of the above compounds of formula I as the sole active principle(s). According to an alternative embodiment, said pharmaceutical composition contains at least one of the above compounds of formula I in association with at least one other active principle. According to a preferred embodiment of the invention, also in combination with the preceding embodiments, the pharmaceutical compositions may be for intravescical, intravenous, topical or oral administration.

The compounds of the invention of formula (I) are conveniently formulated in pharmaceutical compositions using conventional techniques and excipients such as those described in "Remington's Pharmaceutical Sciences Handbook" MACK Publishing, New York, 18th ed., 1990.

A fifth object of the present invention is a therapeutic method for the prevention, reduction of the risk of, amelioration and/or treatment of said diseases associated with activity of BKB1 receptor, as defined above, comprising the administration of the above compound of Formula I in a subject in need thereof.

The compounds of the invention can be administered as the sole active principles or in combination with other therapeutically active compounds.

The administration of the compounds of the invention can be effected by intravesical instillation, by intravenous injection, as a bolus, in dermatological preparations (creams, lotions, sprays and ointments), by inhalation as well as orally in the form of capsules, tablets, syrup, controlled-release formulations and the like.

The average daily dose depends on several factors such as the severity of the disease, the condition, age, sex and weight of the patient. The dose will vary generally from 1 to 1500 mg of compounds of formula (I) per day optionally divided in multiple administrations.

EXAMPLES

The present invention shall be illustrated by means of the following examples which are not construed to be viewed as limiting the scope of the invention
Synthesis of Compounds 1-55 of the Invention.

Compounds of formula 1 wherein R1, R2 and R3 have the identities identified in Table I have been synthesised according to the procedures described in the following examples.

| Compound N. | X | Y | R₁ | R₂ | R₃ |
|---|---|---|---|---|---|
| 1 | O | NH | CH₃ | 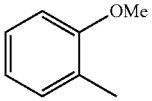 | 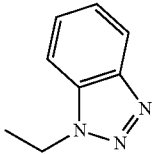 |
| 2 | O | NH | CH₃ | 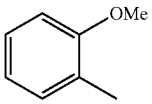 | 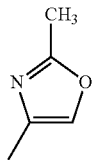 |
| 3 | O | NH | CH₃ | 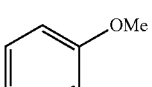 | 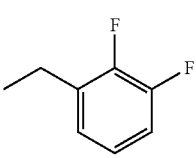 |
| 4 | O | NH | CH₃ | 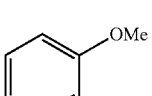 | 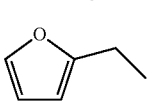 |
| 5 | O | NH | CH₃ | 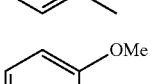 | 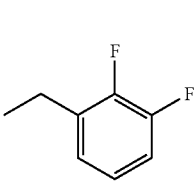 |
| 6 | O | NH | CH₃ | 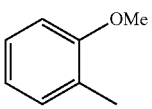 | 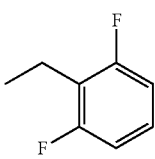 |
| 7 | O | NH | CH₃ | 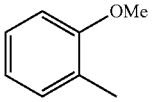 | 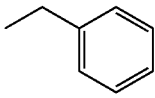 |
| 8 | O | NH | CH₃ | 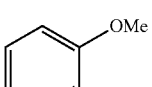 | 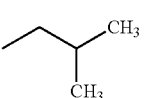 |
| 9 | O | NH | CH₃ | 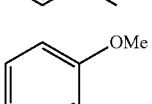 | 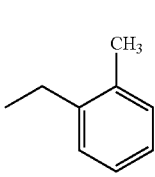 |
| 10 | O | NH | CH₃ | 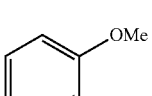 | 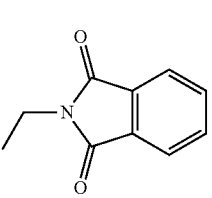 |
| 11 | O | NH | CH₃ | 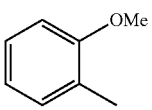 | 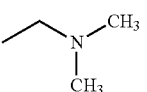 |

-continued

| Compound N. | X | Y | R₁ | R₂ | R₃ |
|---|---|---|---|---|---|
| 12 | O | NH | CH₃ | 2-methoxyphenyl | 4-ethyl-1H-imidazole |
| 13 | O | NH | CH₃ | 2-methoxyphenyl | 2-methoxyphenylethyl |
| 14 | O | NH | CH₃ | 2-methoxyphenyl | n-pentyl |
| 15 | O | NH | CH₃ | 2-methoxyphenyl | cyclopentyl |
| 16 | O | NH | CH₃ | 2-methoxyphenyl | 4-hydroxyphenyl |
| 17 | O | NH | CH₃ | 2-methoxyphenyl | 2-oxopentyl |
| 18 | O | NH | CH₃ | 2-methoxyphenyl | 3-methylphenylethyl |
| 19 | O | NH | CH₃ | 2-methoxyphenyl | 4-methylphenylethyl |
| 20 | O | NH | CH₃ | 2-methoxyphenyl | 4-methylphenyl |
| 21 | O | NH | CH₃ | 2-methoxyphenyl | 4-fluorophenylethyl |
| 22 | O | NH | CH₃ | 2-methoxyphenyl | 4-fluorophenyl |
| 23 | O | NH | CH₃ | 2-methoxyphenyl | 4,4-difluorocyclohexyl |
| 24 | O | NH | CH₃ | 2-methoxyphenyl | n-propyl |

-continued
| Compound N. | X | Y | R₁ | R₂ | R₃ |
|---|---|---|---|---|---|
| 25 | O | NH | CH₃ | 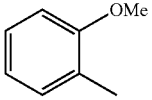 |  |
| 26 | O | NH | CH₃ | 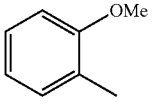 | 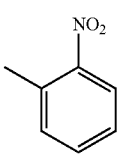 |
| 27 | O | NH | CH₃ | 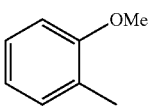 |  |
| 28 | O | NH | CH₃ | 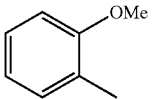 | 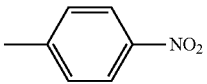 |
| 29 | O | NH | CH₃ | 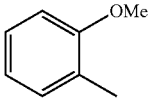 | 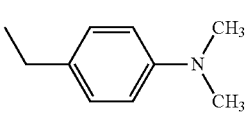 |
| 30 | O | NH | CH₃ | 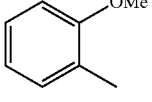 | 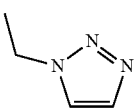 |
| 31 | O | NH | CH₃ | 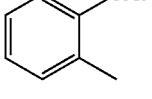 | 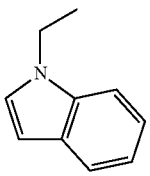 |
| 32 | O | NH | CH₃ | 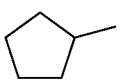 | 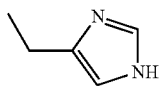 |
| 33 | O | NH | CH₃ | 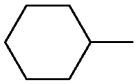 | 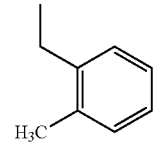 |
| 34 | O | NH | CH₃ | 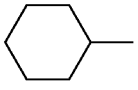 | 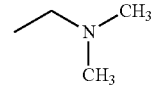 |
| 35 | O | NH | CH₃ | 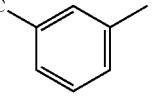 | 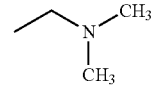 |
| 36 | O | NH | CH₃ | 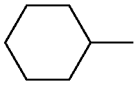 | 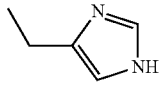 |
| 37 | O | NH | CH₃ | 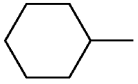 | 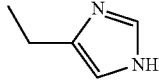 |

-continued
| Compound N. | X | Y | R₁ | R₂ | R₃ |
|---|---|---|---|---|---|
| 38 | O | NH | CH₃ | 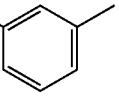 | 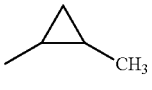 |
| 39 | O | NH | CH₃ | 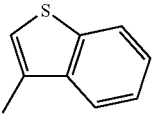 | 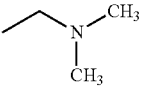 |
| 40 | O | NH | CH₃ | 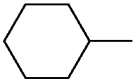 | 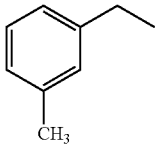 |
| 41 | O | NH | CH₃ | (CH₃CH₂)₂CH₂— | 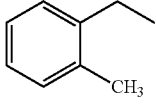 |
| 42 | O | NH | CH₃ | (CH₃CH₂)₂CH₂— | 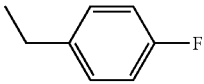 |
| 43 | O | NH | CH₃ | 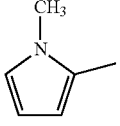 | 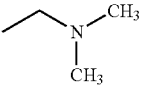 |
| 44 | O | NH | CH₃ | 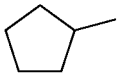 | 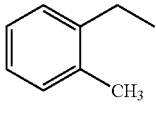 |
| 45 | O | NH | CH₃ | 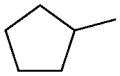 | 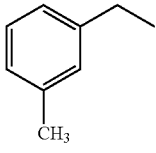 |
| 46 | O | NH | CH₃ | 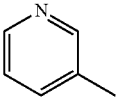 | 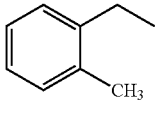 |
| 47 | O | NH | CH₃ | 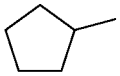 | 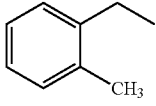 |
| 48 | O | NH | CH₃ | 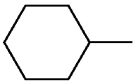 | 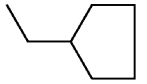 |
| 49 | O | NH | CH₃ | CH₂CH(CH₃)₂ | 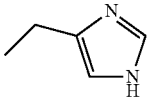 |

-continued

| Compound N. | X | Y | R₁ | R₂ | R₃ |
|---|---|---|---|---|---|
| 50 | O | NH | CH₃ | (CH₃CH₂)₂CH₂— | cyclohexyl |
| 51 | O | NH | CH₃ | cyclopentylmethyl | cyclopentylmethyl |
| 52 | O | NH | cyclopropyl | 2-methoxyphenylmethyl | isobutyl (CH(CH₃)CH₃) |
| 53 | O | NH | CF₃ | 2-methoxyphenylmethyl | ethyl-benzotriazolyl |
| 54 | O | NH | CF₃ | 2-methoxyphenylmethyl | isobutyl (CH(CH₃)CH₃) |
| 55 | NH | O | CH₃ | 2-methoxyphenylmethyl | ethyl-triazolyl |

Materials and Methods

All solvents and reagents were purchased from Sigma-Aldrich, Fluorochem and Alfa Aesar and used without further purification. Nuclear magnetic resonance (NMR) spectra were recorded in the indicated solvent with tetramethylsilane (TMS) as internal standard on a Bruker Avance3 400 MHz instrument. Chemical shifts are reported in parts per million (ppm) relative to the internal standard. Abbreviations are used as follows: s=singlet, d=doublet, t=triplet, q=quartet, m=multiplet, dd=doublets of doublet, br=broad. Coupling constants (J values) are given in hertz (Hz). Analytical HPLC-MS spectra were recorded on a Thermo Finnigan Surveyor coupled with a Thermo Finnigan LCQ DECA XP-PLUS apparatus and equipped with a C18 (10μ, 150 mm×4.6 mm) Phenomenex Gemini reverse phase column. The eluent mixture consisted of 10 mM (pH 4.2) ammonium formate/formic acid buffer and acetonitrile used according the gradient from 90:10 to 10:90 at a flow rate of 1 mL/min. All MS experiments were performed using electrospray ionization (ESI) in positive ion mode. GC-MS spectra were recorded on a Thermo Finnigan TRACE GC apparatus coupled with a Thermo Finnigan DSQ Single Quadrupole as detector and equipped with a Restek Rxi-5 Sil MS (30×0.25 mm) Column fused silica. Instrument method: temperature 60° C. (1 minute hold) to 320° C. at 15° C./min. Flow rate: 1.2 m/min. Carrier gas: He. Injection mode: split (120:1). Injection volume: 1 μL. Preparative HPLC purifications were performed on a Waters Delta Prep HPLC System with Empower software and equipped with a C18 Phenomenex Gemini Axia Packet Column (5μ, 100×21.2 mm). The eluent mixture consisted of 10 mM (pH 3.5) ammonium formate/formic acid buffer and acetonitrile used according the gradient from 90:10 to 10:90 at a flow rate of 10 mL/min. Chiral separations were performed in Supercritical Fluid Chromatography (SFC) [Waters Prep 100 SFC MS Directed System equipped with a CHIRALPAK AD-H Guard Semi-Prep Column (5μ, 250×10 mm); eluent mixture MeOH/CO₂ 20:80, flow rate=5 mL/min].

Optical rotations were recorded on a Perkin Elmer Polarimeter model 241 and the $[\alpha]_D^{25}$ values are given in $10^{-1}$ deg cm² g⁻¹. All reactions were monitored by thin layer chromatography (TLC) carried out on Grace Resolv Davisil silica gel plates 250 μm thick, 60 $F_{254}$, visualized by using UV (254 nm) or stains such as $KMnO_4$, p-anisaldehyde, and ceric ammonium molybdate (CAM). Chromatographic purifications were carried out on silica gel columns with Grace Resolv Davisil silica 60.

General Procedure 1 for the Synthesis of Compounds of Formula II

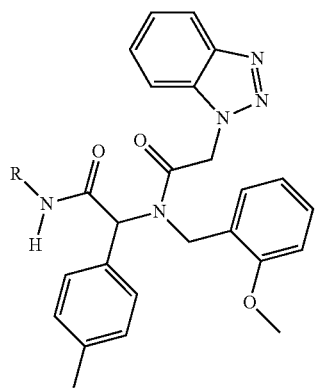

II

Step 1—Preparation of [(1H-benzotriazol-1-ylacetyl) (2-methoxybenzyl)amino](4-methylphenyl)acetic acid (Intermediate A)

To a solution of 4-methylbenzaldehyde (4.38 g, 36 mmol) in 130 mL of acetonitrile at room temperature, 1-(2-methoxyphenyl)methanamine (5 g, 36 mmol) and trimethylsilyl cyanide (5.2 mL, 50 mmol) were added. The mixture was stirred for 16 h at room temperature until the starting materials had been completely consumed as judged by TLC (petroleum ether/ethyl acetate 90:10) and GC analysis. The mixture was quenched with 40 mL of saturated ammonium chloride, stirred for 15 min, added with 100 mL of water and then extracted with ethyl acetate (2×50 mL). The combined organic layers were dried over $Na_2SO_4$, filtered and the solvent was removed under reduced pressure. The residue was purified by flash chromatography on silica gel (petroleum ether/ethyl acetate 90:10) to afford [(2-methoxybenzyl) amino](4-methylphenyl)acetonitrile as a red oil (6.1 g, y=64%). $^1$H NMR ($CDCl_3$) δ (ppm): 7.45 (d, 2H, J=7.3 Hz), 7.33-7.25 (m, 2H), 7.21 (d, 2H, J=7.2 Hz), 6.91-6.85 (m, 2H), 4.79 (s, 1H), 4.03 (d, 1H, J=13.2 Hz), 3.95 (d, 1H, J=13.2 Hz), 3.86 (s, 3H), 2.38 (s, 3H). MS ($ES^{1+}$) m/z: 266.85 (M+1), 240.04 (M-HCN+1).

An Ace pressure tube was charged with 5 g (18.8 mmol) of [(2-methoxybenzyl)amino](4-methylphenyl)acetonitrile and 40 mL of 1,4 dioxane. The solution was cooled at 0° C. and 80 mL of 37% HCl were carefully added to the mixture. The tube was sealed and the mixture was heated at 95° C. for 4 h. The mixture was carefully added to an ice/water mixture and in order to precipitate the product to the acidic mixture was added a 5 M NaOH solution up to pH=5. The solid was isolated by filtration, washed with water and then dried under vacuum at 50° C. to afford [(2-methoxybenzyl)amino](4-methylphenyl)acetic acid as a white solid (4.7 g, y=87%). $^1$H NMR (DMSO-$d_6$) δ (ppm): 7.33-7.26 (m, 4H), 7.17 (d, 2H, J=7.2 Hz), 6.97 (d, 1H, J=7.3 Hz), 6.93 (t, 1H, J=7.2 Hz), 4.20 (s, 1H), 3.81 (s, 2H), 3.71 (s, 3H), 2.31 (s, 3H). MS ($ES^{1+}$) m/z: 286.23 (M+1).

To a cooled (T=0° C.) solution of 1H-benzotriazol-1-ylacetic acid (435 mg, 2.46 mmol) in 10 mL of dry DCM, 2 drops of dry DMF were added. Oxalyl chloride (253 μL, 2.95 mmol) was added dropwise and the reaction was stirred at room temperature for 1 h. The solvent was removed under reduced pressure. The residue was taken up in 4 mL of dry DMF and added dropwise to a solution containing 702 mg (2.46 mmol) of [(2-methoxybenzyl)amino](4-methylphenyl) acetic acid and 360 mg (2.95 mmol) of DMAP dissolved in dry DMF (10 mL). The resulting mixture was allowed to stir for 1 h at room temperature. The solution was slowly added into 20 mL of water, and the formed precipitate was isolated by filtration. The solid was washed with water (5 mL) and dried under vacuum at 50° C. yielding the intermediate A as a white solid (732 mg, y=67%). $^1$H NMR (DMSO-$d_6$) δ (ppm): 12.8 (br s, 1H), 8.12 (d, 1H, J=7.1 Hz), 7.63 (d, 1H, J=7.5 Hz), 7.58 (t, 1H, J=7.1 Hz), 7.43-7.25 (m, 3H), 7.16 (d, 2H, J=7.1 Hz), 7.08 (d, 2H, J=7.0 Hz), 6.95 (m, 2H), 6.00 (d, 1H, J=17.5 Hz), 5.61 (d, 1H, J=17.5 Hz), 5.40 (s, 1H), 4.82 (d, 1H, J=17.8 Hz), 4.57 (d, 1H, J=17.8 Hz), 3.78 (s, 3H), 2.22 (s, 3H). MS ($ES^{1+}$) m/z: 445.34 (M+1).

Step 2—Coupling reaction

Intermediate A (0.05 mmol) was dissolved in dry DCM (2 mL) and 1-chloro-N,N,2-trimethyl-1-propenylamine (TMCE, 0.1 mmol) was dispensed into the solution. The obtained solution was stirred at room temperature for 1 h. Following addition of triethylamine (TEA, 0.1 mmol) and the appropriate amine reagent (0.065 mmol) to the solution the reaction mixture was stirred at room temperature overnight. The reaction was monitored by TLC, generally with the eluent mixture DCM/EtOH 5:1. The reaction mixture was washed with 5% $K_2CO_3$ solution (1 mL) and then with water (1 mL). The organic phase was evaporated with a blow-down evaporator and the so-obtained crude products qualified by HPLC-MS, and further purified by preparative HPLC.

Example 1

2-(1H-benzotriazol-1-yl)-N-(2-methoxybenzyl)-N-{1-(4-methylphenyl)-2-oxo-2-[(tetrahydrofuran-2-ylmethyl)amino]ethyl}acetamide (compound 1)

Following the general procedure I, starting from 1-(tetrahydrofuran-2-yl)methanamine (7.7 μL, 1.5 equiv), compound 1 was obtained as a white solid (18.0 mg, y=70%). $^1$H NMR ($CDCl_3$) δ (ppm): 8.20 (br s, NH) 8.04 (d, 1H, J=8.3 Hz), 7.73-7.48 (m, 2H), 7.45-7.35 (m, 1H), 7.33-7.00 (m, 6H), 6.98-6.87 (m, 2H), 5.92 (s, 1H), 5.77-5.65 (m, 1H), 5.62-5.50 (m, 1H), 4.88-4.77 (m, 1H), 4.75-4.65 (m, 1H), 3.92-3.50 (m, 6H), 3.26-3.00 (m, 2H), 2.22 (s, 3H), 1.90-1.32 (m, 4H). MS ($ES^{1+}$) m/z: 528.10 (M+1).

Example 1a 2-(1H-benzotriazol-1-yl)-N-(2-methoxybenzyl)-N-{[(1R)-1-(4-methylphenyl)]-2-oxo-2-[(2R)-(tetrahydrofuran-2-ylmethyl)amino]ethyl}acetamide (compound 1 (R,R))

Compound 1 (R,R) was obtained as a white solid after preparative SFC-MS purification from diasteroisomeric mixture of compound 1.

Alternatively, the compound was prepared following the general procedure described for intermediate C starting from commercially available (2R)-amino(4-methylphenyl)ethanoic acid and 1-[(2R)-tetrahydrofuran-2-yl]methanamine. The title compound was then prepared following the general procedure 3 starting from 2-methoxybenzaldehyde and 1H-benzotriazol-1-ylacetic acid. $^1$H NMR ($CDCl_3$) δ (ppm): 8.20 (br s, NH) 8.04 (d, 1H, J=8.3 Hz), 7.73-7.48 (m, 2H), 7.45-7.35 (m, 1H), 7.33-7.00 (m, 6H), 6.98-6.87 (m, 2H), 5.92 (s, 1H), 5.72 (d, 1H, J=16.8 Hz), 5.58 (d, 1H, J=16.8 Hz), 4.84 (d, 1H, J=18.4 Hz), 4.70 (d, 1H, J=18.4 Hz), 3.92-3.50 (m, 6H), 3.26-3.00 (m, 2H), 2.22 (s, 3H), 1.90-1.32 (m, 4H). MS ($ES^{1+}$) m/z: 528.34 (M+1). $[α]_D^{25}$=−38.98° (c=0.118 in MeOH).

General Procedure 2 for the Synthesis of Compounds of Formula III

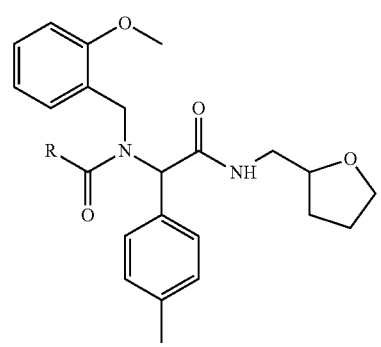

III

Step 1—Preparation of 2-(2-methoxybenzyl)amino-2-(4-methylphenyl)-N-(tetrahydrofuran-2-ylmethyl) acetamide hydrochloride salt (Intermediate B)

A round-bottom flask was charged with [(2-methoxybenzyl)amino](4-methylphenyl)acetic acid (2.19 g, 7.68 mmol), 80 mL of 1,4-dioxane and 16 mL of 1M NaOH solution. To the resulting solution di-tert-butyl dicarbonate ($Boc_2O$, 2.83 g, 13 mmol) were added and the solution stirred at room temperature overnight. The dioxane was removed under reduced pressure; the aqueous solution was adjusted to pH=4 with 3M HCl solution and extracted with ethyl acetate (2×50 mL). The combined organic layers were dried over $Na_2SO_4$, filtered and the solvent removed under reduced pressure yielding [(tert-butoxy carbonyl)(2-methoxybenzyl)amino](4-methylphenyl)acetic acid as a white oil (2.72 g, y=92%) which was used in the following step without further purification. MS ($ES^{1+}$) m/z: 386.37 (M+1).

A round-bottom flask was charged with 2.9 g (7.52 mmol) of [(tert-butoxy carbonyl)(2-methoxybenzyl)amino](4-methylphenyl)acetic acid, 140 mL of dichloromethane and 2.1 mL (15 mmol) of triethylamine. The resulting solution was cooled to 0° C. and 2.3 g (12 mmol) of N-(3-Dimethylaminopropyl)-N'-ethylcarbodiimide hydrochloride (EDC) and 1.62 g (12 mmol) of 1-hydroxybenzotriazole (HOBT) were added. The mixture was stirred for 30 min at 0° C. Then 1.32 mL (12.8 mmol) of 1-(tetrahydrofuran-2-yl)methanamine were added and the solution was allowed to stir at room temperature. After 16 h the reaction was completed (HPLC-MS analysis). The solution was washed with water (2×70 mL), 1M HCl solution (2×50 mL), and brine (2×50 mL). The organic layers were dried over $Na_2SO_4$, filtered and the solvent removed under reduced pressure to afford a brown oil.

The oil was taken up in 30 mL of diethylether and a solution of 4M HCl in dioxane 10 mL) was added. The resulting solution was stirred at room temperature overnight. The solvent was removed under vacuum and the residue diluted with n-hexane (20 mL) and triturated at room temperature for 2 h. The precipitated solid was filtered and dried under vacuum to afford the Intermediate B as a brown solid (2.3 g, y=77%). $^1$H NMR (DMSO-$d_6$) δ (ppm): 9.68 (br s, 2H), 8.72 (br s, 1H), 7.41-7.31 (m, 4H), 7.17 (d, 2H, J=7.1 Hz), 6.95 (d, 1H, J=7.3 Hz), 6.93 (t, 1H, J=7.4 Hz), 4.82 (br s, 1H), 3.90-3.81 (m, 2H), 3.78-3.40 (m, 6H), 3.05 (m, 2H), 2.23 (s, 3H), 1.90-1.11 (m, 4H). MS ($ES^{1+}$) m/z: 369.17 (M+1).

Step 2—Coupling reaction

Intermediate B was dissolved in $CHCl_3$ and was extracted with 5% NaOH aqueous solution and water. The organic phase was dried over anhydrous $MgSO_4$, filtered and the filtrate was concentrated. The reagent carboxylic acid (0.065 mmol) was dissolved in dry DCM (2 mL) and 1-chloro-N,N,2-trimethyl-1-propenylamine (TMCE, 0.13 mmol) was added to the solution. The resulting solution was stirred at room temperature for 1 h. TEA (0.13 mmol) and intermediate B as free amine (0.05 mmol) were added to the solution and the reaction mixture was stirred at room temperature overnight. The reaction was monitored by TLC (n-hexane/ethyl acetate 3:2). The mixture was washed with 5% NaOH aqueous solution (1 mL) then water (1 mL). The organic phase was evaporated with a blow-down evaporator and the crude products were qualified by HPLC-MS, and further purified by preparative HPLC.

Example 2

2-methyl-N-(2-methoxybenzyl)-N-{1-(4-methylphenyl)-2-oxo-2-[(tetrahydrofuran-2-ylmethyl)amino]ethyl}-1,3-oxazole-4-carboxamide (compound 2)

Following the general procedure 2, starting from 2-methyl-1,3-oxazole-4-carboxylic acid, compound 2 was obtained as a dark red oil (16 mg, y=68%). MS ($ES^{1+}$) m/z: 478.61 (M+1).

Example 2a 2-methyl-N-(2-methoxybenzyl)-N-{(1R)-1-(4-methylphenyl)-2-oxo-2-{[(2R)-(tetrahydrofuran-2-ylmethyl)amino]ethyl}-1,3-oxazole-4-carboxamide (compound 2 (R,R))

Compound 2 (R,R) was obtained as a pale yellow solid after preparative SFC-MS purification from diasteroisomeric mixture of compound 2.

Alternatively, the compound was prepared following the procedure described for intermediate C starting from the commercially available (2R)-amino(4-methylphenyl)ethanoic acid and 1-[(2R)-tetrahydrofuran-2-yl]methanamine. The title compound was then prepared following the general procedure 3 starting from 2-methoxybenzaldehyde and 2-methyl-1,3-oxazole-4-carboxylic acid. MS ($ES^{1+}$) m/z: 478.59 (M+1).

Example 3

2-(2,3-difluorophenyl)-N-(2-methoxybenzyl)-N-{1-(4-methyl phenyl)-2-oxo-2-[(tetrahydrofuran-2-ylmethyl)amino]ethyl}acetamide (compound 3)

Following the general procedure 2, starting from (2,3-difluorophenyl)acetic acid, compound 3 was obtained as a orange oil (20 mg, y=78%). MS ($ES^{1+}$) m/z: 523.51 (M+1).

Example 3a 2-(2,3-difluorophenyl)-N-(2-methoxybenzyl)-N-{(1R)-1-(4-methylphenyl)-2-oxo-2-[(2R)-(tetrahydrofuran-2-ylmethyl)amino]ethyl}acetamide (compound 3 (R,R))

Compound 3 (R,R) was obtained as colourless oil after preparative SFC-MS purification from diasteroisomeric mixture of compound 3.

Alternatively, the compound was prepared following the general procedure described for intermediate C starting from commercially available (2R)-amino(4-methylphenyl)ethanoic acid and 1-[(2R)-tetrahydrofuran-2-yl]methanamine. The title compound was then prepared following the general procedure 3 starting from 2-methoxybenzaldehyde and (2,3-difluorophenyl) acetic acid. MS ($ES^{1+}$) m/z: 523.48 (M+1).

Example 4

N-(2-methoxybenzyl)-N-{1-(4-methylphenyl)-2-oxo-2-[(tetrahydrofuran-2-ylmethyl)amino]ethyl}furan-2-carboxamide (compound 4)

Following the general procedure 2, starting from furan-2-carboxylic acid, compound 4 was obtained as a colourless oil (18 mg, y=79%). MS ($ES^{1+}$) m/z: 463.42 (M+1).

Example 4a

N-(2-methoxybenzyl)-N-[(1R)-1-(4-methylphenyl)-2-oxo-2-{[(2R)tetrahydrofuran-2-ylmethyl]amino}ethyl]furan-2-carboxamide (compound 4 (R,R))

Compound 4 (R,R) was obtained as a light sticky solid following preparative SFC-MS purification from the diasteroisomeric mixture of compound 4.

Alternatively, the compound was prepared following the general procedure described for intermediate C starting from commercially available (2R)-amino(4-methylphenyl)ethanoic acid and 1-[(2R)-tetrahydrofuran-2-yl]methanamine. The title compound was then prepared following the general procedure 3 starting from 2-methoxybenzaldehyde and furan-2-carboxylic acid. MS (ES$^{1+}$) m/z: 463.43 (M+1).

Example 5

2-(2,4-difluorophenyl)-N-(2-methoxybenzyl)-N-{1-(4-methylphenyl)-2-oxo-2-[(tetrahydrofuran-2-ylmethyl)amino]ethyl}acetamide (compound 5)

Following the general procedure 2, starting from (2,4-difluorophenyl)acetic acid, compound 5 was obtained as a pale yellow oil (13 mg, y=49%). MS (ES$^{1+}$) m/z: 523.44 (M+1).

Example 6

2-(2,6-difluorophenyl)-N-(2-methoxybenzyl)-N-{1-(4-methylphenyl)-2-oxo-2-[(tetrahydrofuran-2-ylmethyl)amino]ethyl}acetamide (compound 6)

Following the general procedure 2, starting from (2,6-difluorophenyl)acetic acid, compound 6 was obtained as a dark yellow oil (12 mg, y=51%). MS (ES$^{1+}$) m/z: 523.41 (M+1).

Example 6a 2-(2,6-difluorophenyl)-N-(2-methoxybenzyl)-N-{(1R)-1-(4-methylphenyl)-2-oxo-2-[(2R)-(tetrahydrofuran-2-ylmethyl)amino]ethyl}acetamide (compound 6 (R,R))

Compound 6 (R,R) was obtained as red oil after preparative SFC-MS purification from the diasteroisomeric mixture of compound 6.

Alternatively, the compound was prepared following the general procedure described for intermediate C starting from commercially available (2R)-amino(4-methylphenyl)ethanoic acid and 1-[(2R)-tetrahydrofuran-2-yl]methanamine. The title compound was then prepared following the general procedure 3 starting from 2-methoxybenzaldehyde and (2,6-difluorophenyl)acetic acid MS (ES$^{1+}$) m/z: 523.23 (M+1).

Example 7

N-(2-methoxybenzyl)-N-{1-(4-methylphenyl)-2-oxo-2-[(tetrahydrofuran-2-ylmethyl)amino]ethyl}-2-phenylacetamide (compound 7)

Following the general procedure 2, starting from phenylacetic acid, compound 7 was obtained as a glassy solid (19 mg, y=81%). MS (ES$^{1+}$) m/z: 487.52 (M+1).

Example 7a

N-(2-methoxybenzyl)-N-{(1R)-1-(4-methylphenyl)-2-oxo-2-[(2R)-(tetrahydrofuran-2-ylmethyl)amino]ethyl}-2-phenylacetamide (compound 7 (R,R))

Compound 7 (R,R) was obtained as a light sticky solid following preparative SFC-MS purification from the diasteroisomeric mixture of compound 7.

Alternatively, the compound was prepared following the general procedure described for intermediate C starting from commercially available (2R)-amino(4-methylphenyl)ethanoic acid and 1-[(2R)-tetrahydrofuran-2-yl]methanamine. Compound 7a was then prepared following the general procedure 3 starting from 2-methoxybenzaldehyde and phenylacetic acid. MS (ES$^{1+}$) m/z: 487.33 (M+1).

Example 8

3-methyl-N-(2-methoxybenzyl)-N-{(1-(4-methylphenyl)-2-oxo-2-[(tetrahydrofuran-2-ylmethyl)amino]ethyl}butanamide (compound 8)

Following the general procedure 2, starting from 3-methylbutanoic acid, compound 8 was obtained as a light sticky solid (17 mg, y=77%). MS (ES$^{1+}$) m/z: 453.32 (M+1).

Example 8a 3-methyl-N-(2-methoxybenzyl)-N-{[(1R)-1-(4-methylphenyl)]-2-oxo-2-[(2R)-(tetrahydrofuran-2-ylmethyl)amino]ethyl}butanamide (compound 8 (R,R))

Compound 8 (R,R) was obtained as a pale yellow solid after preparative SFC-MS purification from diasteroisomeric mixture of compound 8.

Alternatively, the compound was prepared following the general procedure described for intermediate C starting from commercially available (2R)-amino(4-methylphenyl)ethanoic acid and 1-[(2R)-tetrahydrofuran-2-yl]methanamine. Compound 8a was then prepared following the general procedure 3 starting from 2-methoxybenzaldehyde and 3-methylbutanoic acid. MS (ES$^{1+}$) m/z: 453.13 (M+1).

Example 9

2-(2-methylphenyl)-N-(2-methoxybenzyl)-N-{(1-(4-methylphenyl)-2-oxo-2-[(tetrahydrofuran-2-ylmethyl)amino]ethyl}acetamide (compound 9)

Following the general procedure 2, starting from (2-methylphenyl)acetic acid compound 9 was obtained as a whitish solid (18 mg, y=74%). MS (ES$^{1+}$) m/z: 501.63 (M+1).

Example 10

2-(1,3-dioxoisoindolin-2-yl)-N-(2-methoxybenzyl)-N-{1-(4-methylphenyl)-2-oxo-2-[(tetrahydrofuran-2-ylmethyl)amino]-ethyl}acetamide (compound 10)

Following the general procedure 2, starting from (1,3-dioxo-1,3-dihydro-2H-isoindol-2-yl)acetic acid, compound 10 was obtained as a whitish solid (18 mg, y=65%). MS (ES$^{1+}$) m/z: 556.63 (M+1).

Example 11

2-(dimethylamino)-N-(2-methoxybenzyl)-{1-(4-methylphenyl)-2-oxo-2-[(tetrahydrofuran-2-ylmethyl)amino]ethyl}acetamide (compound 11)

Following the general procedure 2, starting from (dimethylamino)acetic acid compound 11 was obtained as a pale red oil (15 mg, y=71%). MS (ES$^{1+}$) m/z: 454.23 (M+1).

Example 12

2-(1H-imidazol-4-yl)-N-(2-methoxybenzyl)-N-{1-(4-methylphenyl)-2-oxo-2-[(tetrahydrofuran-2-ylmethyl)amino]ethyl}acetamide (compound 12)

Following the general procedure 2, starting from 1H-imidazol-4-ylacetic acid, compound 12 was obtained as a light solid (17 mg, y=70%). MS (ES$^{1+}$) m/z: 477.52 (M+1).

Example 13

2-(2-methoxylphenyl)-N-(2-methoxybenzyl)-N-{(1-(4-methylphenyl)-2-oxo-2-[(tetrahydrofuran-2-ylmethyl)amino]ethyl}acetamide (compound 13)

Following the general procedure 2, starting from (2-methoxyphenyl)acetic acid, compound 13 was obtained as a yellow solid (19 mg, y=76%). MS (ES$^{1+}$) m/z: 517.51 (M+1).

Example 14

N-(2-methoxybenzyl)-N-{1-(4-methylphenyl)-2-oxo-2-[(tetrahydrofuran-2-ylmethyl)amino]ethyl}pentanamide (compound 14)

Following the general procedure 2, starting from pentanoic acid, compound 14 was obtained as a colourless oil (17 mg, y=74%). MS (ES$^{1+}$) m/z: 453.56 (M+1).

Example 15

N-(2-methoxybenzyl)-N-{1-(4-methylphenyl)-2-oxo-2-[(tetrahydrofuran-2-ylmethyl)amino]ethyl}cyclopentanecarboxamide (compound 15)

Following the general procedure 2, starting from cyclopentanecarboxylic acid, compound 15 was obtained as a colourless oil (16 mg, y=71%). MS (ES$^{1+}$) m/z: 467.53 (M+1).

Example 16

4-hydroxy-N-(2-methoxybenzyl)-N-{1-(4-methylphenyl)-2-oxo-2-[(tetrahydrofuran-2-ylmethyl)amino]ethyl}benzamide (compound 16)

Following the general procedure 2, starting from 4-hydroxybenzoic acid, compound 16 was obtained as a dark yellow solid (20 mg, y=81%). MS (ES$^{1+}$) m/z: 489.12 (M+1).

Example 17

4-oxo-N-(2-methoxybenzyl)-N-{1-(4-methylphenyl)-2-oxo-2-[(tetrahydrofuran-2-ylmethyl)amino]ethyl}pentanamide (compound 17)

Following the general procedure 2, starting from 4-oxopentanoic acid, compound 17 was obtained as a orange glassy solid (19 mg, y=81%). MS (ES$^{1+}$) m/z: 467.33 (M+1).

Example 18

2-(3-methylphenyl)-N-(2-methoxybenzyl)-N-{(1-(4-methylphenyl)-2-oxo-2-[(tetrahydrofuran-2-ylmethyl)amino]ethyl}acetamide (compound 18)

Following the general procedure 2, starting from (3-methylphenyl)acetic acid, compound 18 was obtained as a red oil (18 mg, y=70%). MS (ES$^{1+}$) m/z: 501.32 (M+1).

Example 19

2-(4-methylphenyl)-N-(2-methoxybenzyl)-N-{(1-(4-methylphenyl)-2-oxo-2-[(tetrahydrofuran-2-ylmethyl)amino]ethyl}acetamide (compound 19)

Following the general procedure 2, starting from (4-methylphenyl)acetic acid, compound 19 was obtained as a pale yellow solid (19 mg, y=74%). MS (ES$^{1+}$) m/z: 501.33 (M+1).

Example 20

4-methyl-N-(2-methoxybenzyl)-N-{1-(4-methylphenyl)-2-oxo-2-[(tetrahydrofuran-2-ylmethyl)amino]ethyl}benzamide (compound 20)

Following the general procedure 2, starting from 4-methylbenzoic acid, compound 20 was obtained as a light yellow oil (19 mg, y=78%). MS (ES$^{1+}$) m/z: 487.42 (M+1).

Example 21

2-(4-fluorophenyl)-N-(2-methoxybenzyl)-N-{(1-(4-methylphenyl)-2-oxo-2-[(tetrahydrofuran-2-ylmethyl)amino]ethyl}acetamide (compound 21)

Following the general procedure 2, starting from (4-fluorophenyl)acetic acid, compound 21 was obtained as a orange solid (13 mg, y=51%). MS (ES$^{1+}$) m/z: 505.39 (M+1).

Example 22

4-fluoro-N-(2-methoxybenzyl)-N-{1-(4-methylphenyl)-2-oxo-2-[(tetrahydrofuran-2-ylmethyl)amino]ethyl}benzamide (compound 22)

Following the general procedure 2, starting from 4-fluorobenzoic acid, compound 22 was obtained as a brown solid (13 mg, y=55%). MS (ES$^{1+}$) m/z: 491.47 (M+1).

Example 23

4,4-difluoro-N-(2-methoxybenzyl)-N-{1-(4-methylphenyl)-2-oxo-2-[(tetrahydrofuran-2-ylmethyl)amino]ethyl}cyclohexanecarboxamide (compound 23)

Following the general procedure 2, starting from 4,4-difluorocyclohexanecarboxylic acid, compound 23 was obtained as a dark brown solid (21 mg, y=81%). MS (ES$^{1+}$) m/z: 515.23 (M+1).

Example 24

N-(2-methoxybenzyl)-N-{1-(4-methylphenyl)-2-oxo-2-[(tetrahydrofuran-2-ylmethyl)amino]ethyl}propanamide (compound 24)

Following the general procedure 2, starting from propanoic acid, compound 24 was obtained as a light yellow oil (18 mg, y=83%). MS (ES$^{1+}$) m/z: 425.42 (M+1).

Example 25

N-(2-methoxybenzyl)-N-{1-(4-methylphenyl)-2-oxo-2-[(tetrahydrofuran-2-ylmethyl)amino]ethyl}cyclobutanecarboxamide (compound 25)

Following the general procedure 2, starting from cyclobutanecarboxylic acid, compound 25 was obtained as a white solid (18 mg, y=78%). MS (ES$^{1+}$) m/z: 451.36 (M+1).

Example 26

N-(2-methoxybenzyl)-2-nitro-N-{1-(4-methylphenyl)-2-oxo-2-[(tetrahydrofuran-2-ylmethyl)amino]ethyl}benzamide (compound 26)

Following the general procedure 2, starting from 2-nitrobenzoic acid, compound 26 was obtained as a dark red solid (16 mg, y=61%). MS (ES$^{1+}$) m/z: 518.51 (M+1).

Example 27

N-(2-methoxybenzyl)-N-{1-(4-methylphenyl)-2-oxo-2-[(tetrahydrofuran-2-ylmethyl)amino]ethyl}cyclopropanecarboxamide (compound 27)

Following the general procedure 2, starting from cyclopropanecarboxylic acid, compound 27 was obtained as a pale green oil (15 mg, y=69%). MS (ES$^{1+}$) m/z: 437.51 (M+1).

Example 28

N-(2-methoxybenzyl)-4-nitro-N-{1-(4-methylphenyl)-2-oxo-2-[(tetrahydrofuran-2-ylmethyl)amino]ethyl}benzamide (compound 28)

Following the general procedure 2, starting from 4-nitrobenzoic acid, compound 28 was obtained as a pale orange solid (19 mg, y=72%). MS (ES$^{1+}$) m/z: 518.42 (M+1).

Example 29

2-[(4-dimethylamino)phenyl]-N-(2-methoxybenzyl)-N-{1-(4-methylphenyl)-2-oxo-2-[(tetrahydrofuran-2-ylmethyl)amino]ethyl}acetamide (compound 29)

Following the general procedure 2, starting from [4-(dimethylamino)phenyl]acetic acid, compound 29 was obtained as a pale red oil (23 mg, y=86%). MS (ES$^{1+}$) m/z: 530.53 (M+1).

Example 30

N-(2-methoxybenzyl)-N-{1-(4-methylphenyl)-2-oxo-2-[(tetrahydrofuran-2-ylmethyl)amino]ethyl}-2-(1H-1,2,3-triazol-1-yl)acetamide (compound 30)

Intermediate B as free amine (0.054 g, 0.15 mmol) was dissolved in dry THF (2 mL) and bromoacetyl chloride (1.2 eq., 15 µL, 0.18 mmol) in dry THF (0.5 mL) and DMAP (0.021 g, 0.17 mmol) were added to the flask. The mixture was stirred 5 h at room temperature and the reaction was monitored by HPLC-MS. The ionization data for the product showed the halogen exchange in the product during the reaction. The solvent was evaporated under reduced pressure and the crude dissolved in DCM (20 mL). The organic layer was washed with 1M HCl solution (5 mL) and brine (5 mL) then dried over Na$_2$SO$_4$. The chloride derivative was obtained as a yellow oil (0.060 g, y=90%) and qualified by HPLC-MS. The product was used in the following step without further purification. MS (ES$^{1+}$) m/z: 445.03 (M+1), 467.21 (M+23), 483.16 (M+38).

1H-1,2,3-triazole (10 µL, 0.18 mmol) and 1,8-diazabicyclo[5.4.0]undec-7-ene (DBU, 45 µL, 0.3 mmol) were dissolved in dry THF (0.9 mL) and was stirred 10 minutes at room temperature. Then 2-chloro-N-(2-methoxybenzyl)-N-[2-[(tetrahydrofuran-2-ylmethyl)-1-(4-methylphenyl)-2-oxoethyl]acetamide (0.060 g, 0.15 mmol) was added to the mixture and the reaction stirred overnight at room temperature (as monitored by HPLC-MS). The solvent was evaporated under reduced pressure and the product was purified by preparative HPLC. Compound 30 was obtained as a red oil (0.052 g, y=73%). $^1$H NMR (CD$_3$OD) δ (ppm): 8.00 (s, 1H), 7.77 (s, 1H), 7.30-6.85 (m, 8H), 5.75 (s, 1H), 5.62 (d, 1H, J=16.6 Hz), 5.40 (d, 1H, J=16.6 Hz), 4.53-4.51 (m, 2H), 3.98-3.51 (m, 8H), 3.50-3.20 (m, 1H), 2.25 (s, 3H), 1.95-1.45 (m, 3H), 0.95-0.80 (m, 1H). MS (ES$^{1+}$) m/z: 478.13 (M+1), 500.32 (M+23).

Example 30a

N-(2-methoxybenzyl)-N-{(1R)-1-(4-methylphenyl)-2-oxo-2-[(2R)-(tetrahydrofuran-2-ylmethyl)amino]ethyl}-2-(1H-1,2,3-triazol-1-yl)acetamide (compound 30 (R,R))

Compound 30 (R,R) was obtained as a yellow solid after preparative SFC-MS purification from diastereoisomeric mixture of compound 30.

Alternatively, the compound was prepared following the general procedure described for intermediate C starting from commercially available (2R)-amino-(4-methylphenyl)ethanoic acid and 1-[(2R)-tetrahydrofuran-2-yl]methanamine. Compound 30 (R,R) was prepared following the general procedure 3 starting from 2-methoxybenzaldehyde and 1H-1,2,3-triazol-1-ylacetic acid. MS (ES$^{1+}$) m/z: 478.02 (M+1).

Example 31

2-(1H-indol-1-yl)-N-(2-methoxybenzyl)-N-{1-(4-methylphenyl)-2-oxo-2-[(tetrahydrofuran-2-ylmethyl)amino]ethyl}acetamide (compound 31)

1H-indole (0.351 g, 3.00 mmol) was dissolved in dry THF (9 mL) and cooled at 0° C. for 10 minutes under argon atmosphere. To the cooled solution 2.2 equivalents of NaH (0.156 g, 6.5 mmol) and 1.05 equivalents of tert-butyl bromoacetate (0.46 mL, 3.15 mmol) were added. The mixture was allowed to reach room temperature and stirred 3.5 h. To complete the transformation the reaction was heated at 70° C. for 2 h. The reaction was monitored by GC-MS. The mixture was quenched with water (5 mL) and the product was extracted with ethyl acetate (3×50 mL). The product was purified by flash chromatography using n-hexane/ethyl acetate 95:5 as eluent and isolated as a yellow oil (0.543 g, y=78%). $^1$H NMR (CDCl$_3$) δ (ppm): 7.66 (dt, 1H, J=7.9, 0.9

Hz), 7.28 (d, 1H, J=7.9 Hz), 7.25 (dd, 1H, J=6.6, 1.1 Hz), 7.15 (dd, 1H, J=6.6, 1.1 Hz), 7.10 (d, 1H, J=3.2 Hz), 6.58 (dd, 1H, J=3.2, 0.9 Hz), 4.77 (s, 2H), 1.45 (s, 9H).

To a solution of tert-butyl 1H-indol-1-ylacetate (0.3 g, 1.29 mmol) in MeOH (2 mL) KOH (0.65 g, 11.6 mmol) and water (70 μL) were added. The suspension was stirred at room temperature for 3 h (monitored by TLC, eluent n-hexane/ethyl acetate 9:1, and by HPLC-MS). The mixture was diluted in water (10 mL) and the aqueous phase was washed with Et$_2$O (10 mL) to eliminate the t-BuOH from the mixture. The aqueous phase was acidified up to pH=3 with 1M HCl solution then the acid extracted with ethyl acetate (3×20 mL). The organic layers were dried over Na$_2$SO$_4$ and the solvent was evaporated under reduced pressure. The product was isolated as a white solid (0.191 g, y=84%) and qualified by HPLC-MS. The product was used in the following step without further purification. MS (ES$^{1+}$) m/z: 176.17 (M+1).

1H-indol-1-ylacetic acid (0.104 g, 0.594 mmol) was dissolved in dry DCM (3 mL) and the solution was cooled to 0° C. To the mixture oxalyl chloride (51 μL, 0.594 mmol) and catalytic dry DMF (2 μL) were added; the mixture was stirred 30 minutes a 0° C. then the reaction was allowed to reach room temperature and stirred 1 hour. The transformation was monitored by HPLC-MS. The solvent was evaporated under reduced pressure and the acyl chloride obtained was used without further purification.

A solution of 2-(2-methoxybenzyl)amino-2-(4-methylphenyl)-N-(tetrahydrofuran-2-ylmethyl)acetamide (intermediate B as free amine, 0.048 g, 0.13 mmol) in dry DMF (3 mL) was cooled to 0° C. then 1H-indol-1-ylacetyl chloride (0.594 mmol) and DMAP (0.016 g, 0.13 mmol) were added to the mixture. The mixture was stirred 30 minutes at 0° C. then overnight at room temperature (monitored by TLC, eluent n-hexane/ethyl acetate/MeOH 8:1.5:0.5, and by HPLC-MS). The reaction was quenched with water (5 mL) and the product was extracted with ethyl acetate (3×20 mL). The organics were dried over Na$_2$SO$_4$ and the solvent was evaporated under reduced pressure. The product was purified by flash chromatography and isolated as a yellow oil (0.057 g, y=83%). $^1$H NMR (CDCl$_3$) δ (ppm): 7.61 (d, 1H, J=7.7 Hz), 7.29-7.13 (m, 5H), 7.11-7.02 (m, 5H), 6.92 (dt, 1H, J=7.7, 0.9 Hz), 6.82 (d, 1H, J=8.2 Hz), 6.54 (d, 1H, J=3.2 Hz), 6.02 (br s, NH), 5.82 (s, 1H), 4.97 (d, 1H, J=16.7 Hz), 4.86 (d, 1H, J=16.7 Hz), 4.78 (d, 1H, J=18.0 Hz), 4.62 (d, 1H, J=18.0 Hz), 3.94-3.86 (m, 1H), 3.80 (s, 3H), 3.78-3.58 (m, 2H), 3.55-3.45 (m, 1H), 3.28-3.18 (m, 1H), 2.31 (s, 3H), 1.95-1.75 (m, 3H), 1.60-1.40 (m, 1H). MS (ES$^{1+}$) m/z: 526.84 (M+1), 548.30 (M+23), 564.19 (M+38).

General Procedure 3 for the Synthesis of Compounds of Formula IV

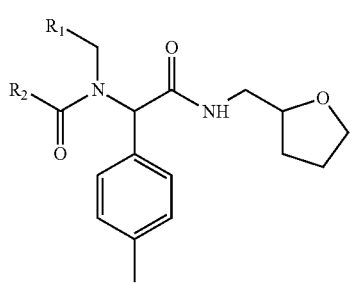

IV

Step 1—Preparation of 1-(4-methylphenyl)-2-oxo-2-[(tetrahydrofuran-2-ylmethyl)amino]ethanaminium chloride (Intermediate C)

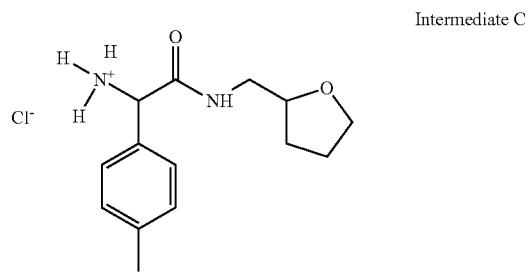

Intermediate C

A one-necked round-bottom flask was charged with amino (4-methylphenyl)acetic acid (10 g, 60.5 mmol), 1,4-dioxane (300 mL) and 1M NaOH (170 mL). To the resulting solution di-tert-butyl dicarbonate (19.8 g, 90.8 mmol) was added and the solution stirred at room temperature overnight. The dioxane was removed under reduced pressure and the aqueous solution was adjusted to pH 4 with 3M HCl and the product extracted with ethyl acetate (2×50 mL). The combined organic layers were dried over Na$_2$SO$_4$, filtered and the solvent removed under reduced pressure to afford [(tert-butoxycarbonyl)amino](4-methylphenyl)acetic acid as a white solid (15.2 g, y=95%). $^1$H NMR (DMSO-d$_6$) δ (ppm): 7.44 (d, 1H, J=7.4 Hz), 7.27 (d, 2H, J=7.2 Hz), 7.14 (d, 2H, J=7.3 Hz), 5.03 (d, 1H, J=5.4 Hz), 2.28 (s, 3H), 1.38 (s, 9H). MS (ES$^{1+}$) m/z: 266.42 (M+1). A one-necked round-bottom flask was charged with [(tert-butoxycarbonyl)amino](4-methylphenyl) acetic acid (16 g, 60.5 mmol), DCM (500 mL) and triethylamine (16.7 mL, 121 mmol). The resulting solution was cooled to 0° C. and N-(3-dimethylaminopropyl)-N-ethylcarbodiimide hydrochloride (EDC, 13.9 g, 72.6 mmol) and 1-hydroxybenzotriazole (HOBT, 9.8 g, 72.6 mmol) were added. The mixture was stirred for 40 min at 0° C. Then 1-(tetrahydrofuran-2-yl)methanamine (10.6 mL, 103 mmol) was added and the solution stirred at room temperature overnight. After 18 h the reaction was complete (HPLC-MS analysis). The solution was washed with water (2×150 mL), 1M HCl (2×150 mL), and brine (2×150 mL). The organic layers were dried over Na$_2$SO$_4$, filtered and the solvent was removed under reduced pressure to afford a white solid which was taken up in 100 mL of n-hexane and triturated at room temperature for 2 h. The precipitate was filtered and dried under vacuum at 50° C. for 4 h. The solid was dissolved in 100 mL of 1,4-dioxane and 25 mL of 4M HCl solution in dioxane were added. The resulting solution was stirred at room temperature overnight. After solvent removal under vacuum, the residue was taken up in diethyl ether (40 mL) and triturated at room temperature for 2 h. The precipitate was filtered and dried under vacuum at 50° C. to afford Intermediate C as a white solid (11.6 g, y=67% over two steps). $^1$H NMR (DMSO-d$_6$) δ (ppm): 8.75 (br s, 3H), 7.45 (d, 2H, J=7.5 Hz), 7.22 (d, 2H, J=7.4 Hz), 4.91 (br s, 1H), 3.90-3.51 (m, 4H), 3.22-3.04 (m, 2H), 2.28 (s, 3H), 1.85-1.26 (m, 4H). MS (ES$^{1+}$) m/z: 249.04 (M+1).

Step 2—Synthesis of Compounds of Formula IV

To a solution of intermediate C (1 mmol) in dry DCM (5 mL), TEA (2.5 mmol) and the appropriate aldehyde (1.1 mmol) were added. The mixture was stirred at room temperature for 30 minutes. Then NaBH(OAc)$_3$ was added to the mixture. The so-obtained reaction mixture was further stirred at room temperature overnight (monitored by TLC with eluent n-hexane/ethyl acetate 3:2). The mixture was washed with water (3 mL), 1M HCl (3 mL) and brine (3 mL). The organic phase was evaporated under reduced pressure and the so-obtained crude product was qualified by HPLC-MS, and used without any purification in the following reaction step.

The reagent carboxylic acid (0.065 mmol) was dissolved in dry DCM (2 mL) then 1-chloro-N,N,2-trimethyl-1-propenylamine (TMCE, 0.13 mmol) was dispensed to the solution. The so-obtained mixture was stirred at room temperature for 1 h. TEA (0.13 mmol) and the appropriate amine scaffold (0.05 mmol) were added to the solution then the reaction mixture stirred at room temperature overnight (HPLC-MS analysis). The mixture was washed with 5% NaOH aqueous solution (1 mL) and water (1 mL). The organic phase was evaporated with a blow-down evaporator and the so-obtained crude products were qualified by HPLC-MS, and purified by preparative HPLC to afford the desired compounds.

Example 32

N-(cyclopentylmethyl)-2-(1H-imidazol-4-yl)-N-{1-(4-methylphenyl)-2-oxo-2-[(tetrahydrofuran-2-ylmethyl)amino]ethyl}acetamide (compound 32)

Following the general procedure 3, starting from cyclopentanecarbaldehyde and 1H-imidazol-4-ylacetic acid, compound 32 was obtained as a white solid (15 mg, y=70%). MS (ES$^{1+}$) m/z: 439.49 (M+1).

Example 33

N-(cyclohexylmethyl)-2-(2-methylphenyl)-N-{1-(4-methylphenyl)-2-oxo-2-[(tetrahydrofuran-2-ylmethyl)amino]ethyl}acetamide (compound 33)

Following the general procedure 3 starting from cyclohexanecarbaldehyde and (2-methylphenyl)acetic acid, compound 33 was obtained as an orange oil (16 mg, y=68%). MS (ES$^{1+}$) m/z: 477.69 (M+1).

Example 34

N-(cyclohexylmethyl)-2-(dimethylamino)-N-{1-(4-methylphenyl)-2-oxo-2-[(tetrahydrofuran-2-ylmethyl)amino]ethyl}acetamide (compound 34)

Following the general procedure 3, starting from cyclohexanecarbaldehyde and (dimethylamino)acetic acid, compound 34 was obtained as a red oil (19 mg, y=88%). MS (ES$^{1+}$) m/z: 430.38 (M+1).

Example 35

2-(dimethylamino)-N-(3-methylbenzyl)-N-{1-(4-methylphenyl)-2-oxo-2-[(tetrahydrofuran-2-ylmethyl)amino]ethyl}acetamide (compound 35)

Following the general procedure 3, starting from 3-methylbenzaldehyde and (dimethylamino)acetic acid, compound 35 was obtained as a whitish solid (19 mg, y=86%). MS (ES$^{1+}$) m/z: 438.39 (M+1).

Example 36

N-(cyclohexylmethyl)-2-(1H-imidazol-4-yl)-N-{1-(4-methylphenyl)-2-oxo-2-[(tetrahydrofuran-2-ylmethyl)amino]ethyl}acetamide (compound 36)

Following the general procedure 3, starting from cyclohexanecarbaldehyde and 1H-imidazol-4-ylacetic acid, compound 36 was obtained as a red oil (16 mg, y=71%). MS (ES$^{1+}$) m/z: 453.68 (M+1).

Example 37

N-(cyclohexyl methyl)-2-phenyl-N-{1-(4-methylphenyl)-2-oxo-2-[(tetrahydrofuran-2-ylmethyl)amino]ethyl}acetamide (compound 37)

Following the general procedure 3, starting from cyclohexanecarbaldehyde and phenylacetic acid, compound 37 was obtained as a white oil (17 mg, y=73%). MS (ES$^{1+}$) m/z: 463.61 (M+1).

Example 38

2-methyl-N-(3-methylbenzyl)-N-{1-(4-methylphenyl)-2-oxo-2-[(tetrahydrofuran-2-ylmethyl)amino]ethyl}cyclopropanecarboxamide (compound 38)

Following the general procedure 3, starting from 3-methylbenzaldehyde and 2-methylcyclopropanecarboxylic acid, compound 38 was obtained as a whitish solid (19 mg, y=86%). MS (ES$^{1+}$) m/z: 435.69 (M+1).

Example 39

N-(1-benzothiophen-3-ylmethyl)-2-(dimethylamino)-N-{1-(4-methylphenyl)-2-oxo-2-[(tetrahydrofuran-2-ylmethyl)amino]ethyl}acetamide (compound 39)

Following the general procedure 3, starting from 1-benzothiophene-3-carbaldehyde and (dimethylamino)acetic acid, compound 39 was obtained as an orange solid (13 mg, y=55%). MS (ES$^{1+}$) m/z: 480.68 (M+1).

Example 40

N-(cyclohexylmethyl)-2-(3-methylphenyl)-N-{1-(4-methylphenyl)-2-oxo-2-[(tetrahydrofuran-2-ylmethyl)amino]ethyl}acetamide (compound 40)

Following the general procedure 3, starting from cyclohexanecarbaldehyde and (3-methylphenyl)acetic acid, compound 40 was obtained as a white solid (17 mg, y=72%). MS (ES$^{1+}$) m/z: 477.71 (M+1).

Example 41

N-(2-ethyl butyl)-2-(2-methylphenyl)-N-{1-(4-methylphenyl)-2-oxo-2-[(tetrahydrofuran-2-ylmethyl)amino]ethyl}acetamide (compound 41)

Following the general procedure 3, starting from 2-ethylbutanaldehyde and (2-methylphenyl)acetic acid, compound 41 was obtained as a red oil (17 mg, y=74%). MS (ES$^{1+}$) m/z: 465.60 (M+1).

Example 42

N-(2-ethyl butyl)-2-(4-fluorophenyl)-N-{1-(4-methylphenyl)-2-oxo-2-[(tetrahydrofuran-2-ylmethyl) amino]ethyl}acetamide (compound 42)

Following the general procedure 3, starting from 2-ethylbutanaldehyde and (4-fluorophenyl)acetic acid, compound 42 was obtained as a yellow solid (18 mg, y=77%). MS (ES$^{1+}$) m/z: 469.51 (M+1).

Example 43

2-(dimethylamino)-N-[(1-methyl-1H-pyrrol-2-yl)methyl]-N-{1-(4-methylphenyl)-2-oxo-2-[(tetrahydrofuran-2-ylmethyl)amino]ethyl}acetamide (compound 43)

Following the general procedure, starting from 1-methyl-1H-pyrrole-2-carbaldehyde and (dimethylamino)acetic acid, compound 43 was obtained as a yellow solid (17 mg, y=82%). MS (ES$^{1+}$) m/z: 427.56 (M+1).

Example 44

N-(cyclopentylmethyl)-2-(2-methylphenyl)-N-{1-(4-methylphenyl)-2-oxo-2-[(tetrahydrofuran-2-ylmethyl)amino]ethyl}acetamide (compound 44)

Following the general procedure 3, starting from cyclopentanecarbaldehyde and (2-methylphenyl)acetic acid, compound 44 was obtained as a white solid (16 mg, y=71%). MS (ES$^{1+}$) m/z: 463.59 (M+1).

Example 45

N-(cyclopentylmethyl)-2-(3-methylphenyl)-N-{1-(4-methylphenyl)-2-oxo-2-[(tetrahydrofuran-2-ylmethyl)amino]ethyl}acetamide (compound 45)

Following the general procedure 3, starting from cyclopentanecarbaldehyde and (3-methylphenyl)acetic acid, compound 45 was obtained as a white solid (17 mg, y=74%). MS (ES$^{1+}$) m/z: 463.58 (M+1).

Example 46

2-(2-methylphenyl)-N-(pyridin-3-ylmethyl)-N-{1-(4-methylphenyl)-2-oxo-2-[(tetrahydrofuran-2-ylmethyl)amino]ethyl}acetamide (compound 46)

Following the general procedure 3, starting from pyridine-3-carbaldehyde and (2-methylphenyl)acetic acid, compound 46 was obtained as a white solid (18 mg, y=76%). MS (ES$^{1+}$) m/z: 472.58 (M+1).

Example 47

N-(cyclopentylmethyl)-N-{1-(4-methylphenyl)-2-oxo-2-[(tetrahydrofuran-2-yl)methylamino]ethyl}2-phenylacetamide (compound 47)

Following the general procedure 3, starting from cyclopentanecarbaldehyde and phenylacetic acid, compound 47 was obtained as a brown solid (16 mg, y=71%). MS (ES$^{1+}$) m/z: 449.68 (M+1).

Example 48

N-(cyclohexylmethyl)-2-cyclopentyl-N-{1-(4-methylphenyl)-2-oxo-2-[(tetrahydrofuran-2-ylmethyl) amino]ethyl}acetamide (compound 48)

Following the general procedure 3, starting from cyclohexanecarbaldehyde and cyclopentylacetic acid, compound 48 was obtained as a reddish oil (9 mg, y=42%). MS (ES$^{1+}$) m/z: 455.41 (M+1).

Example 49

2-(1H-imidazol-4-yl)-N-(2-methylpropyl)-N-{1-(4-methylphenyl)-2-oxo-2-[(tetrahydrofuran-2-ylmethyl)amino]ethyl}acetamide (compound 49)

Following the general procedure 3, starting from 2-methylpropanal and 1H-imidazol-4-ylacetic acid, compound 49 was obtained as a white solid (10 mg, y=47%). MS (ES$^{1+}$) m/z: 413.31 (M+1).

Example 50

N-(2-ethyl butyl)-N-{1-(4-methylphenyl)-2-oxo-2-[(tetrahydrofuran-2-ylmethyl)amino] ethyl}cyclohexanecarboxamide (compound 50)

Following the general procedure 3, starting from 2-ethylbutanaldehyde and cyclohexanecarboxylic acid, compound 50 was obtained as a yellow oil (19 mg, y=84%). MS (ES$^{1+}$) m/z: 443.45 (M+1).

Example 51

2-cyclopentyl-N-cyclopentylmethyl-N-{1-(4-methylphenyl)-2-oxo-2-[(tetrahydrofuran-2-ylmethyl) amino]ethyl}acetamide (compound 51)

Following the general procedure 3, starting from cyclopentanecarbaldehyde and cyclopentylacetic acid, compound 51 was obtained as a white oil (16 mg, y=71%). MS (ES$^{1+}$) m/z: 441.58 (M+1).

Example 52

N-(2-methoxybenzyl]-N-[1-(4-cyclopropylphenyl)-2-oxo-2-[(tetrahydrofuran-2-yl)methylamino]ethyl)-3-methylbutanamide (compound 52)

In a two necked round bottom flask, 4-bromobenzaldehyde (1.00 g, 5.40 mmol) was dissolved in CH$_3$CN (15 mL) at room temperature then 1.4 equivalents of 1-(2-methoxyphenyl)methanamine (0.99 mL, 7.56 mmol) and 1.3 equivalents of trimethylsilyl cyanide (TMSCN, 1.08 mL, 8.64 mmol) were added to the solution and the mixture was stirred 3 h at room temperature. The transformation was monitored by TLC with an eluent of n-hexane/ethyl acetate 9:1 and by HPLC-MS. To complete the transformation the reaction was stirred at room temperature overnight. The solvent was evaporated under reduced pressure and the residue taken up with ethyl acetate (100 mL) then the organic layer was washed whit NaHCO$_3$ aqueous saturated solution (10 mL), NH$_4$Cl aqueous saturated solution (10 mL) and with brine (10 mL). The product was purified by flash chromatography and obtained as a light yellow solid (1.40 g, y=78%). $^1$H NMR (CDCl$_3$) δ (ppm): 7.56 (d, 2H, J=8.5 Hz), 7.47 (d, 2H, J=8.5

Hz), 7.32 (dd, 1H, J=7.7, 1.7 Hz), 7.28 (dd, 1H, J=7.7, 1.7 Hz), 6.96 (dt, 1H, J=7.4, 1.0 Hz), 6.91 (dd, 1H, J=7.4, 1.0 Hz), 4.78 (s, 1H), 3.97 (s, 2H), 3.87 (s, 3H). MS (EI) m/z: 304.22 [M-HCN].

(4-Bromophenyl)[(2-methoxybenzyl)amino]acetonitrile (0.607 g, 1.83 mmol) was dissolved in dry 1,4-dioxane (6 mL) and 37% HCl (6 mL) was added to the solution. The reaction was stirred 2 h at reflux and was monitored by HPLC-MS. The solvent was evaporated under reduced pressure and the product was purified by flash chromatography (eluent n-hexane/ethyl acetate/MeOH 6:3:1). The product was obtained as a white solid (0.53 g, y=82%). MS (ES$^{1+}$) m/z: 350.08 (M+1) 100%, 351.96 (M+2) 97.9%.

A solution of (4-bromophenyl)[(2-methoxybenzyl)amino] acetic acid (0.530 g, 1.51 mmol) in dry DMF (2.6 mL) was cooled to 0° C. then 1.5 equivalents of DMAP (0.277 g, 2.26 mmol) and 1.7 equivalents of 3-methylbutanoyl chloride (0.32 mL, 2.56 mmol) were added to the mixture. The reaction was allowed to reach room temperature and stirred overnight. The transformation was monitored by HPLC-MS and by TLC with an eluent of n-hexane/ethyl acetate/MeOH 6:3:1. The mixture was diluted in water (10 mL) and the product extracted twice with ethyl acetate (2×50 mL). The organics were washed with brine (10 mL) and dried over Na$_2$SO$_4$. The product was purified by flash chromatography and the product was isolated as a yellow oil (0.450 g, y=69%). MS (ES$^{1+}$) m/z: 434.10 (M+1) 100%, 436.02 (M+2) 97.9%.

[(2-Methoxybenzyl)(3-methylbutanoyl)amino](4-bromophenyl)acetic acid (0.328 g, 0.755 mmol) was dissolved in dry DCM (10 mL) then the solution was cooled to 0° C. using an ice bath. To the solution 1.6 equivalents of 1-hydroxybenzotriazole (HOBT, 0.163 g, 1.21 mmol) and 1.6 equivalents of N-(3-dimethylaminopropyl)-N'-ethylcarbodiimide hydrochloride (EDC, 0.231 g, 1.21 mmol) were added and the mixture was stirred at 0° C. for 30 minutes. To the stirred and cooled mixture 2 equivalents of TEA (0.21 mL, 1.51 mmol) and 1.5 equivalents of 1-(tetrahydrofuran-2-yl)methanamine (0.12 mL, 1.13 mmol) were added and the reaction was allowed to reach room temperature and stirred overnight. The transformation was monitored by HPLC-MS and by TLC with an eluent of n-hexane/ethyl acetate 5:5. The solvent was evaporated under reduced pressure and the crude taken up with ethyl acetate (30 mL); the organic layer was washed with NaHCO$_3$ aqueous saturated solution (10 mL) and with brine (10 mL) then dried over Na$_2$SO$_4$. The product was purified by flash chromatography and was obtained as a white solid (0.344 g, y=88%). MS (ES$^{1+}$) m/z: 516.91 (M+1) 100%, 518.82 (M+2) 97.9%.

N-(2-methoxybenzyl)-{1-(4-bromophenyl)-2-oxo-2-[(tetrahydrofuran-2-ylmethyl)amino]ethyl}-3-methylbutanamide (0.086 g, 0.166 mmol) was dissolved in dry toluene (2 mL), then K$_3$PO$_4$ (0.143 g, 0.67 mmol) and cyclopropyl boronic acid (0.022 g, 0.25 mmol) were added to the solution. Argon was bubbled into the solution to eliminate the oxygen from the solvent then 7% mol of Pd(PPh$_3$)$_4$ (0.016 g, 0.013 mmol) and water (43 μL) were added. The solution was irradiated in a MW-apparatus up to 120° C. for 15 minutes and the transformation was monitored by HPLC-MS. The solution was diluted in water (10 mL) and the product was extracted with ethyl acetate (3×20 mL). The combined organics were washed with brine (5 mL) and dried over Na$_2$SO$_4$. The product was purified by flash chromatography with an eluent of n-hexanelethyl acetate 1:1 and compound 52 was obtained as a white solid (0.057 g, y=$^{72}$%). $^1$H NMR (CDCl$_3$) δ (ppm): 7.38-7.32 (m, 1H), 7.28-7.10 (m, 4H), 6.97-6.91 (m, 1H), 6.89-6.82 (m, 1H), 6.78-6.72 (m, 1H), 6.24-5.97 (m, 1H), 5.60-5.48 (m, 1H), 4.71-4.62 (m, 1H), 4.57-4.45 (m, 1H), 3.93 (br s, 1H), 3.83-3.65 (m, 6H), 3.54-3.46 (m, 1H), 3.32-3.19 (m, 1H), 2.40-1.45 (m, 9H), 1.05-0.82 (m, 7H), 0.73-0.50 (m, 2H). MS (ES$^{1+}$) m/z: 478.97 (M+1).

Example 53

2-(1H-benzotriazol-1-yl)-N-(2-methoxybenzyl)-N-{1-(4-trifluoromethylphenyl)-2-oxo-2-[(tetrahydrofuran-2-ylmethyl)amino]ethyl}acetamide (compound 53)

Following the procedure used for the synthesis of intermediate B, 2-[(2-methoxybenzyl)amino]-N-(tetrahydrofuran-2-ylmethyl)-2-[4-(trifluoromethyl)phenyl]acetamide was synthesized starting from 4-(trifluoromethyl)benzaldehyde, then compound 53 was obtained as a glassy brown solid by amide bond formation with 1H-benzotriazol-1-ylacetyl chloride (23 mg, y=76%). $^1$H NMR (CDCl$_3$) δ (ppm): 8.09 (d, 1H, J=8.3 Hz), 7.58-7.45 (m, 4H), 7.44-7.35 (m, 3H), 7.30-7.15 (m, 2H), 6.93 (t, 1H, J=7.6 Hz), 6.81 (d, 1H, J=7.6 Hz), 6.20-6.05 (br s, NH), 5.87-5.41 (m, 2H), 4.89-4.72 (m, 2H), 3.85 (s, 3H), 3.77-3.60 (m, 2H), 3.53-3.43 (m, 1H), 3.26-3.13 (m, 1H), 1.98-1.75 (m, 4H), 1.60-1.40 (m, 1H), 0.95-0.80 (m, 1H). MS (ES$^{1+}$) m/z: 582.11 (M+1).

Example 54

N-[(2-methoxybenzyl]-N-{1-[4-(trifluoromethyl) phenyl]-2-oxo-2-[(tetrahydrofuran-2-yl)methylamino]ethyl}3-methylbutanamide (compound 54)

Following the procedure used for the synthesis of intermediate B, 2-[(2-methoxybenzyl)amino]-N-(tetrahydrofuran-2-ylmethyl)-2-[4-(trifluoromethyl)phenyl]acetamide was synthesized starting from 4-(trifluoromethyl)benzaldehyde, then compound 54 was obtained as a dark orange oil by amide bond formation with isovaleryl chloride (31 mg, y=78%). $^1$H NMR (CDCl$_3$) δ (ppm): 7.49-7.41 (m, 4H), 7.20 (t, 1H, J=7.7 Hz), 7.11 (t, 1H, J=8.3 Hz), 6.85 (t, 1H, J=7.7 Hz), 6.74 (d, 1H, J=8.3 Hz), 6.33-6.18 (br s, NH), 5.62 (s, 1H), 4.69 (d, 1H, J=16.2 Hz), 4.58 (d, 1H, J=16.2 Hz), 4.00-3.87 (m, 1H), 3.85-3.65 (m, 5H), 3.60-3.48 (m, 1H), 3.28-3.17 (m, 1H), 2.40-2.20 (m, 3H), 2.00-1.75 (m, 3H), 1.65-1.48 (m, 1H), 0.98 (s, 6H). MS (ES$^{1+}$) m/z: 506.93 (M+1).

Example 55

N-(2-methoxybenzyl)-N-{(1R)-1-(4-methylphenyl)-2-oxo-2-[(2R)-(pyrrolidin-2-ylmethyl)amino]ethyl}-2-(1H-1,2,3-triazol-1-yl)acetate (compound 55 (R,R))

A one-necked round-bottom flask was charged with 0.362 g (0.9 mmol) of [(tert-butoxy carbonyl)(2-methoxybenzyl) amino](4-methylphenyl)acetic acid, 18 mL of dry dichloromethane and 0.26 mL (1.88 mmol) of triethylamine. The resulting solution was cooled to 0° C. and 0.288 g (1.5 mmol) of N-(3-Dimethylaminopropyl)-N'-ethylcarbodiimide hydrochloride (EDC) and 0.202 g (1.5 mmol) of 1-hydroxybenzotriazole (HOBT) were added. The mixture was stirred for 30 min at 0° C. Then 0.296 mL (3 mmol) of (R)-2-Pyrrolidinemethanol were added and the solution was allowed to stir at room temperature for 15 min and for 2 h at 40° C. After the reaction was complete as judged by HPLC-MS analysis, the solution was washed with water (2×10 mL), 1M HCl solution (2×10 mL), and brine (2×10 mL). The organic layers were dried over $Na_2SO_4$, filtered and the solvent was removed under reduced pressure to afford a yellow oil.

The oil was taken up in 10 mL of diethylether and 2 mL 4M HCl solution in dioxane were added. The solution was stirred at room temperature for 2 h. The solvent was removed under vacuum and the residue was diluted with n-hexane (10 mL) and triturated at room temperature for 1 h. The solid was filtered and dried under vacuum at 50° C. to afford the title compound as a dark yellow oil (0.113 g, y=34%). $^1$H NMR (DMSO-$d_6$) δ (ppm): 9.63 (br s, 2H), 7.40-7.33 (m, 4H), 7.16 (d, 2H, J=7.1 Hz), 6.95 (d, 1H, J=7.3 Hz), 6.94 (t, 1H, J=7.4 Hz), 4.87 (br s, 1H), 3.88-3.80 (m, 3H), 3.71-3.42 (m, 6H), 3.00 (m, 2H), 2.21 (s, 3H), 1.80-1.21 (m, 4H). MS (ES1+) m/z: 369.11 (M+1).

The compound (0.113 mg, 0.31 mmol) was dissolved in dry THF (2 mL) then 1 equivalent of bromoacetyl chloride (26 μL, 0.31 mmol) in dry THF (0.5 mL) and DMAP (37 mg, 0.3 mmol) were added to the flask. The mixture was stirred 5 h at room temperature and the transformation was monitored by HPLC-MS. The ionization data for the product showed the halogen exchange in the product during the reaction. The solvent was evaporated under reduced pressure and the crude dissolved in DCM (5 mL). The organic layer was washed with 1M HCl solution (5 mL) and brine (5 mL) then dried over $Na_2SO_4$. The chloride derivative was obtained as a yellow oil and was qualified by HPLC-MS. The product was used in the following step without further purification. 1H-1,2,3-triazole (52 μL, 0.9 mmol) and 1,8-diazabicyclo[5.4.0]undec-7-ene (DBU, 46 μL, 0.31 mmol) were dissolved in dry THF (2 mL) and was stirred 10 minutes at room temperature. Then 2-chloro-N-(1R)-(2-methoxybenzyl)-N-[(2R)-2-[(pyrrolidin-2-ylmethyl)-1-(4-methylphenyl)-2-oxoethyl]acetate (0.138 g, 0.31 mmol) was added to the mixture and the reaction was stirred overnight at room temperature. The transformation was monitored by HPLC-MS. The solvent was evaporated under reduced pressure and the product was purified by preparative HPLC. The product was obtained as a yellow oil (0.083 g, y=56%). $^1$H NMR (CD3OD) δ (ppm): 7.71 (s, 1H), 7.29-6.80 (m, 8H), 5.73 (s, 1H), 5.65 (d, 1H, J=16.6 Hz), 5.41 (d, 1H, J=16.6 Hz), 4.43-4.50 (m, 2H), 3.91-3.61 (m, 9H), 3.47-3.22 (m, 1H), 2.22 (s, 3H), 1.95-1.45 (m, 3H), 0.95- 0.78 (m, 1H). MS (ES1+) m/z: 478.05 (M+1).

Example 55a

N-(2-methoxybenzyl)-N-{(1S)-1-(4-methylphenyl)-2-oxo-2-[(2R)-(pyrrolidin-2-ylmethyl)amino]ethyl}-2-(1H-1,2,3-triazol-1-yl)acetate (Compound 55 (R,R))

Following the procedure described for compound 55 and starting from commercially available (2S)-amino(4-methylphenyl)acetic acid and (R)-2-Pyrrolidinemethanol, the title compound was obtained as light yellow oil (22 mg, y=55%). 1H NMR (CD3OD) δ (ppm): 7.68 (s, 1H), 7.22-6.71 (m, 8H), 5.71 (s, 1H), 5.61 (d, 1H, J=16.9 Hz), 5.40 (d, 1H, J=16.8 Hz), 4.63-4.50 (m, 2H), 3.91-3.61 (m, 9H), 3.43-3.21 (m, 1H), 2.20 (s, 3H), 1.94-1.43 (m, 3H), 0.89- 0.71 (m, 1H). MS ($ES^{1+}$) m/z: 478.23 (M+1).

Example 56

Biological Evaluation

Calcium Mobilization Assay (FLIPR)—Human (IMR-90) lung fibroblast cells expressing native BKB1 receptors were harvested by trypsinization and seeded into black wall/clear bottom 96-well plates (Costar 3904; Corning Life Sciences, Acton, Mass.) at approximately 13,000 cells/well. After 1 day incubation, cells were treated with human IL-1 (0.35 ng/ml) in 10% FBS/MEM for 2 h to up-regulate BKB1 receptors. Induced cells were loaded with fluorescent calcium indicator by incubation with 2.3 M Fluo-4/acetoxymethyl ester (Invitrogen) at 37° C. for 1.5 h in the presence of an anion transport inhibitor (2.5 mM probenecid in 1% FBS/MEM). Extracellular dye was removed by washing with assay buffer (2.5 mM probenecid, 0.1% BSA in 20 mM HEPES/HBSS without bicarbonate or phenol red, pH 7.5) and cell plates were kept in the dark until used. Test compounds were assayed at eight concentrations in triplicate. Addition of test compounds to the cell plate and incubation for 5 min at 35° C., followed by the addition of 2 to 8 nM final BKB1 agonist desArg$^{10}$-kallidin (DAKD, 3×$EC_{50}$) was carried out in the fluorimetric imaging plate reader (FLIPR; Molecular Devices) while continuously monitoring calcium-dependent fluorescence.

Responses for BKB2 receptors were measured in IMR-90 cells in an identical manner except that IL-1 treatment was not necessary and bradykinin (0.7 nM final; 3×$EC_{50}$) replaced DAKD as agonist.

As shown in the following Table I, the compounds 1-55 of the invention were tested in the above described assay, as a mixture of stereoisomers (indicated in Table II as mix) or as single stereoisomers (configuration specified in Table II), and were found active in inhibiting calcium mobilization in the $IC_{50}$ range of 0.1-15 M in the BKB1 receptors-expressing cells. The same compounds were found inactive when tested on the BKB2 receptors-expressing cells biological assay.

TABLE II $IC_{50}$-values of examples

| Compound- | $IC_{50}$ (μM) |
|---|---|
| 1 (mix) | 1.9 |
| 1 (R,R) | 0.043 |
| 2 (R,R) | 0.063 |
| 3 (R,R) | 0.540 |
| 4 (R,R) | 0.358 |
| 5 (mix) | 1.4 |
| 6 (R,R) | 0.456 |
| 7 (R,R) | 0.200 |
| 8 (mix) | 0.418 |
| 8 (R,R) | 0.134 |
| 9 (mix) | 0.3 |
| 10 (mix) | 0.3 |
| 11 (mix) | 10 |
| 12 (mix) | 0.098 |
| 13 (mix) | 0.3 |
| 14 (mix) | 0.3 |
| 15 (mix) | 0.3 |
| 16 (mix) | 1 |
| 17 (mix) | 1.2 |
| 18 (mix) | 0.3 |
| 19 (mix) | 1.4 |
| 20 (mix) | 6.1 |
| 21 (mix) | 3.5 |
| 22 (mix) | 8.7 |
| 23 (mix) | 8.4 |
| 24 (mix) | 13.2 |
| 25 (mix) | 15.7 |
| 26 (mix) | 14.4 |
| 27 (mix) | 15 |
| 28 (mix) | 3 |
| 29 (mix) | 2.1 |
| 30 (mix) | 0.068 |
| 30 (R,R) | 0.011 |
| 31 (mix) | 0.268 |
| 32 (mix) | 0.8 |
| 33 (mix) | 1.7 |

TABLE II-continued

IC$_{50}$-values of examples

| Compound- | IC$_{50}$ (μM) |
|---|---|
| 34 (mix) | 1.1 |
| 35 (mix) | 1.7 |
| 36 (mix) | 13.8 |
| 37 (mix) | 6.2 |
| 38 (mix) | 12.7 |
| 39 (mix) | 1.2 |
| 40 (mix) | 5.1 |
| 41 (mix) | 4.3 |
| 42 (mix) | 9.6 |
| 43 (mix) | 9.5 |
| 44 (mix) | 12.6 |
| 45 (mix) | 13.1 |
| 46 (mix) | 11.7 |
| 47 (mix) | 9.8 |
| 48 (mix) | 15 |
| 49 (mix) | 14.7 |
| 50 (mix) | 14.2 |
| 51 (mix) | 13 |
| 52 (mix) | 0.063 |
| 53 (mix) | 0.297 |
| 54 (mix) | 0.528 |
| 55 (R,R) | 0.0757 |
| 55 (S,R) | 0.12 |

Example 57

Evaluation of In Vivo Activity (Compound 8 (R,R))-Chronic Constriction Model of Pain Animals An evaluation of the in vivo activity of compound 8 (R,R) was performed by testing the inhibition potential in mechanical allodynia using the chronic constriction model of pain.

Male Sprague-Dawley (SD) derived rats weighing 180±20 g (at arrival) were provided by BioLasco Taiwan (under Charles River Laboratories Technology Licensee). Space allocation for 5 animals per cage was 45×23×21 cm and maintained in a controlled temperature (20-24° C.) and humidity (50%-80%) environment with 12 hours light/dark cycles for at least three days in Ricerca Biosciences, LLC (Taipei, Taiwan) Laboratory prior to use. Free access to standard lab chow for rats [MF-18 (Oriental Yeast Co., Ltd., Japan)] and tap water was granted. All aspects of this work including housing, experimentation and disposal of animals were performed in general accordance with the Guide for the Care and Use of Laboratory Animals (National Academy Press, Washington, D. C., 2010).

Neuropathic pain behavior was induced by ligation of the sciatic nerve according to the method described by Bennett and Xie [Bennett G. J. and Xie Y. K. A peripheral mononeuropathy in rat that produces disorders of pain sensation like those seen in man, Pain, (1988) 33:87-107]. Briefly, rats were anaesthetized under pentobarbital (50 mg/kg, 5 mL/kg, IP) anesthesia and the sciatic nerve was exposed at mid-thigh level. Four ligatures (4-0 chromic gut suture), about 1 mm apart, were loosely tied around the nerve. The animals were then housed individually in cages with soft bedding for 7 days before testing for mechanical allodynia. Testing for the development of tactile allodynia was performed between 7-14 days following operation. The force-filaments used were of the magnitude of 3.61 (0.4 g), 3.84 (0.6 g), 4.08 (1.0 g), 4.31 (2.0 g), 4.56 (4.0 g), 4.74 (6.0 g), 4.93 (8.0 g), and 5.18 (15.0 g).

Rats were pre-selected for experimentation only if the pain threshold 7-14 days after nerve ligation had clear presence of allodynia. Rats which did not respond between the forces of 0.4-8 g were excluded from the study. The rats were randomized to treatment groups.

The rats had access to food and water up to the time of the experiment, and then were placed under inverted Plexiglas cages on a wire mesh rack and allowed to acclimate for 20 to 30 minutes. Allodynia was evaluated using the Chaplin "up/down" method using von Frey hairs [Chaplan, S. R, Bach, F. W., Pogrel, J. W., Chung, J. M. and Yaksh, T. L. Quantitative assessment of tactile allodynia in the rat paw. J. Neurosci. Methods (1994) 53: 55-63]. Compound 8a was dissolved in 10% EtOH/50% PEG400/Saline and administered intravenously (IV) at 3, 10 and 30 mg/kg to groups of 12 SD rats. The dosing volume was 2 mL/kg.

The mechanical allodynia using the up/down method was performed 30 minutes before and at 1, 2 and 3 hour(s) after intravenous injection of the vehicle or test substances. The investigator performing the behavioral testing was blind to treatment (a different investigator dosed the animals).

The allodynia test started with the monofilament handle marked 4.31 (2.0 g), applying the nylon filament perpendicularly to the plantar surface of the appropriate hind paw from underneath the wire mesh floor. This step was repeated 3 to 5 times in succession covering a broad plantar area on the same animal or until there was a response. Brisk withdrawal or paw flinching was considered a positive response and the next weaker monofilament was chosen and applied in the same manner as described above. Static movement of the paw (excluding locomotion) was considered a negative response and the next stronger monofilament was chosen and applied in the same manner.

Analysis

The threshold of response of the treated rats was compared to respective vehicle treated rats; two-way ANOVA followed by Bonferroni's test was used for comparison between vehicle and treated groups. Also, un-paired Student's t-test was used to compare the values between the gabapentin control group and the gabapentin-treated group. The delta change value at each time point was also calculated. One-way ANOVA followed by Dunnett's test was used for comparison between the test substance-treated groups and vehicle control. P<0.05 is considered significant.

Results

The inhibitory activity of compound 8 (R,R) at 30 mg/kg IV was associated with a significant reversal of CCI-induced mechanical allodynia in rats at 1 hour (37% of inhibition), but not at 2 and 3 hours post-dose.

Example 58

ADME Evaluation

In three of the rats tested in Example 56, indicated as R1, R3 and R3, also the pharmacokinetic profile of compound 8 (R,R) was evaluated. The results are summarised in Tables III to IV and in FIGS. 1-4.

Table III shows the pharmacokinetic parameters of compound 8 (R,R) administered at a dose of 10 mg/kg by oral gavage.

Table IV shows the concentration of compound 8 (R,R) in the plasma or brain, expressed in ng/ml, after intravenous (IV) administration at a dose of 7.5 mg/kg Table V shows the pharmacokinetic parameters of compound 8 (R,R) following intravenous (IV) administration at a dose of 7.5 mg/kg.

Table VI shows the concentration of compound 8 (R,R) in the plasma, expressed in ng/ml, after intravenous (IV) administration at a dose of 7.5 mg/kg.

Figure 2:
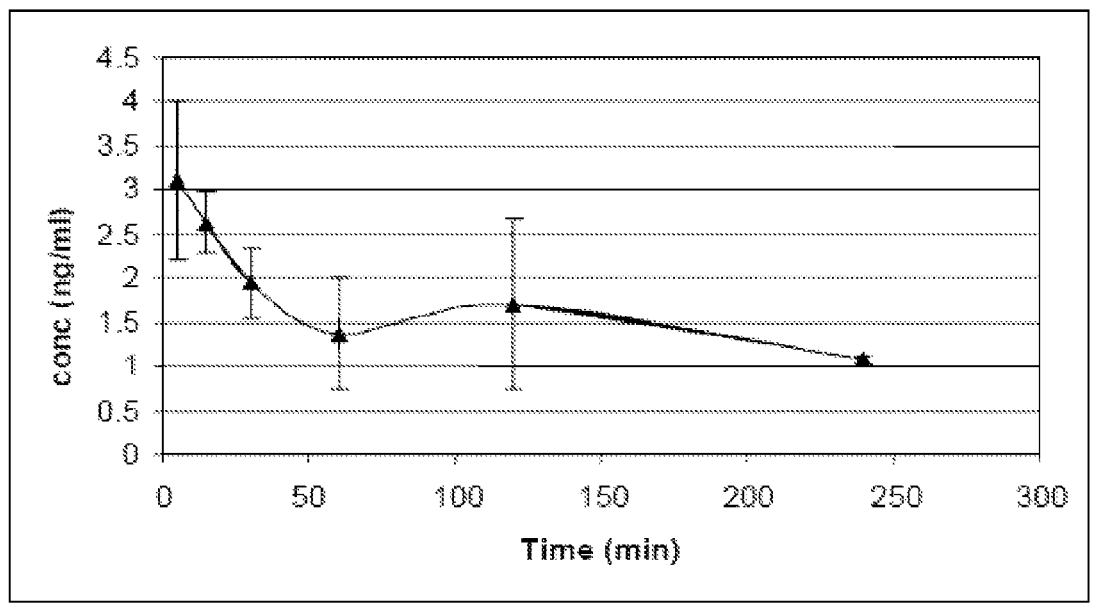
FIG. 2 shows the plasma concentrations, expressed in ng/ml, of compound 8 (R,R) over time after oral administration as an average of the values obtained by each of the three subject tested.

FIGS. 1 and 2 show the plasma concentrations, expressed in ng/ml, of compound 8 (R,R) over time after oral administration for each of the three subjects tested (FIG. 1) and as an average (FIG. 2).

Figure 3:
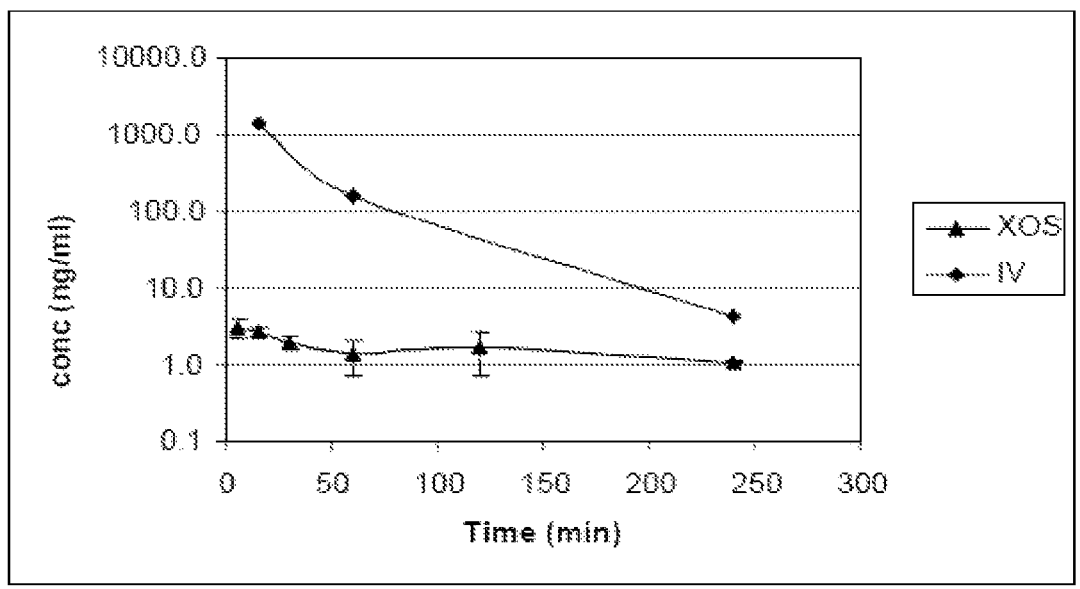
FIG. 3 shows the comparison between the plasma concentrations, expressed in ng/ml, of compound 8 (R,R) over time after IV (IV) and oral administration (XOS).

FIG. 3 shows the comparison between the plasma concentrations, expressed in ng/ml, of compound 8 (R,R) over time after IV (IV) and oral administration (XOS).

Figure 4:
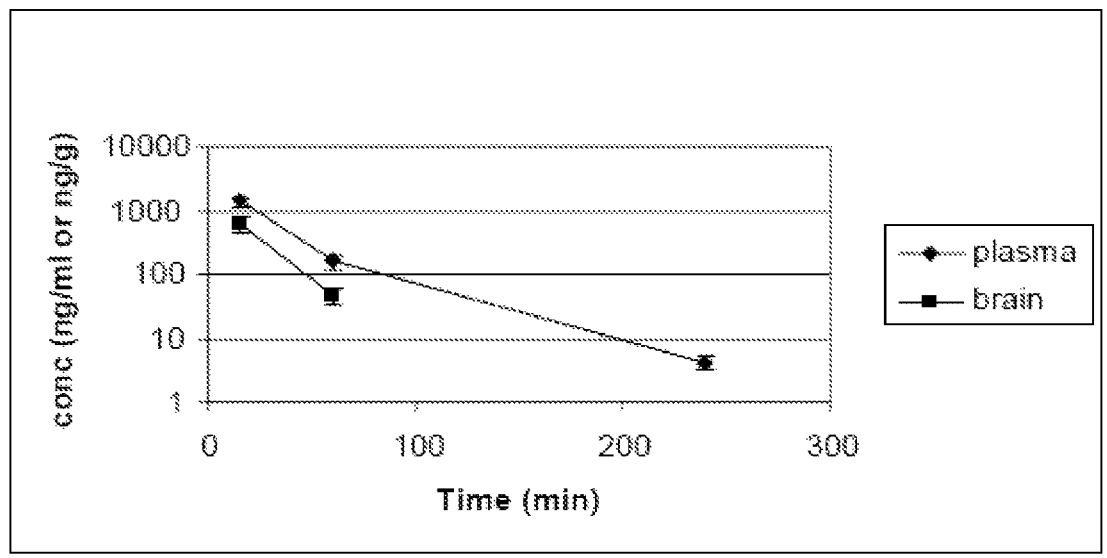
FIG. 4 shows the kinetic profile in plasma or brain after IV administration for brain penetration assessment.

FIG. 4 shows the kinetic profile in plasma or brain after IV administration for brain penetration assessment. Table VII shows the degradation rate of compound 8 (R,R) in the liver.

In tables III and V, T1/2 means the half-time of the compound, Tmax means the time at which the concentration of the compound reaches the maximum level, Cmax means the maximal concentration, Tlast means the latest time-point at which the concentration of the compound can be measured, Clast means the concentration at the latest time-point at which the concentration of the compound can be measured, AUClast means the area under the curve at the latest time-point at which the concentration of the compound can be measured, AUCinf_obs means the area under the curve which is infinitely extrapolated and MRTlast means the mean residence time at the latest time-point at which the concentration of the compound can be measured.

In tables IV and VI, LLOQ means lower limit of quantification.

TABLE III

Pharmacokinetic parameters of
compound 8 (R,R) at 10 mg/kg oral gavage

| XOS | Rat 1 | Rat 2 | Rat 3 | Average | Standard deviation |
|---|---|---|---|---|---|
| T½ (min) | 344.8 | 191.1 | 70.2 | 202.0 | 137.6 |
| Tmax (min) | 5.0 | 15.0 | 5.0 | 8.3 | 5.8 |
| Cmax (ng/ml) | 4.0 | 3.0 | 3.3 | 3.4 | 0.5 |
| Tlast (min) | 240 | 240 | 120 | 200.0 | 69.3 |
| Clast (ng/ml) | 1.1 | 1.1 | 1.0 | 1.1 | — |
| AUClast (min * ng/ml) | 340.1 | 517.3 | 155.6 | 337.7 | 180.8 |
| AUCINF_obs(min * ng/ml) | 862.4 | 820.6 | 256.9 | 646.6 | 338.1 |
| MRTlast (min) | 101.2 | 104.1 | 47.7 | 84.3 | 31.8 |

TABLE IV

Levels of compound 8 (R,R) in plasma
and brain after IV administration at 7.5 mg/kg

| Time | R1 | R2 | R3 | Average | SD |
|---|---|---|---|---|---|
| | Plasma level ng/ml | | | | |
| 15 | 1595 | 1137.5 | 1472 | 1401.5 | 236.8 |
| 60 | 123.2 | 157.3 | 205.2 | 161.9 | 41.2 |
| 240 | 4.05 | 3.35 | 5.2 | 4.2 | 0.9 |
| 480 | <LLOQ | <LLOQ | <LLOQ | <LLOQ | |
| | Brain level ng/g | | | | |
| 15 | 619.3 | 446.05 | 839.85 | 635.1 | 197.4 |
| 60 | 62.15 | 34.65 | 49.5 | 48.8 | 13.8 |
| 240 | <LLOQ | <LLOQ | <LLOQ | <LLOQ | |
| 480 | <LLOQ | <LLOQ | <LLOQ | <LLOQ | |

TABLE V

Pharmacokinetic parameters
of compound 8 (R,R) at 7.5 mg/kg after
IV administration for brain penetration assessment

| | Plasma | Brain |
|---|---|---|
| T½ (min) | 12.5 | Missing |
| Tmax (min) | 15 | 15 |
| Cmax (ng/ml) | 1401.5 | 635.1 |
| Tlast (min) | 240 | 60 |
| Clast (ng/ml) | 4.2 | 48.8 |
| AUClast (min * ng/ml) | 72253 | 31355.1 |
| MRTlast (min) | 15.9 | 11.2 |

TABLE VI

Compound 8 (R,R) plasma levels after
oral administration expressed as ng/ml

| Time min | Rat1 | Rat2 | Rat3 | Average | SD |
|---|---|---|---|---|---|
| | | ng/ml | | | |
| 5 | 4.0 | 2.2 | 3.3 | 3.1 | 0.9 |
| 15 | 2.7 | 3.0 | 2.3 | 2.6 | 0.4 |
| 30 | 1.8 | 2.4 | 1.7 | 2.0 | 0.4 |
| 60 | 1.3 | 2.1 | 0.8 | 1.4 | 0.6 |
| 120 | 1.3 | 2.8 | 1.0 | 1.7 | 1.0 |
| 240 | 1.1 | 1.1 | <LLOQ | 1.1 | 0.1 |
| 480 | <LLOQ | <LLOQ | <LLOQ | <LLOQ | |

As can be seen from the above, compound 8a showed a very poor absorption after oral administration compared to the intravenous exposure, resulting in a Cmax about 3 ng/ml and in an oral bioavailability of 0.16%.

Brain penetration was performed by IV administration at 7.5 mg/kg. Brain penetration resulted about 43% calculated as average on the AUC ratio. Plasma and brain levels are reported in Table IV and FIG. 4.

Metabolic stability of compound 8 (R,R) was also determined in rat wistar liver microsomes in the in the presence of NADPH.

The concentration of the compound 8 (R,R) was 1 µM and microsomes 0.5 mg/ml in phosphate buffer 0.1M pH 7.4 with NADPH.

The degradation of the substrates was measured in duplicate by LC/MS/MS during six time points of incubation. The intrinsic clearance ($CL_{int}$) in the presence of NADPH was 851 L/min/mgP.

The invention claimed is:

1. A method for the amelioration and/or treatment of a pain-related disorder or disease comprising administering to a subject in need thereof a compound of formula (I):

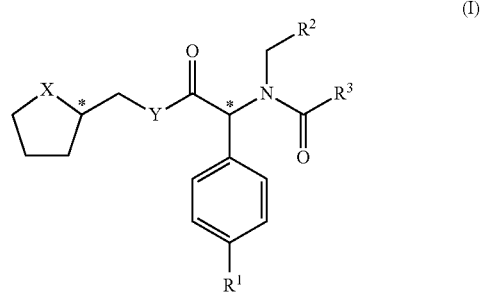

or a pharmaceutically acceptable salts thereof, wherein
X and Y are different one from the other and are O or NH;

R¹ is selected from the group consisting of
C₁-C₆-alkyl; C₃-C₆-cycloalkyl and halo C₁-C₃-alkyl;
R² is selected from the group consisting of:
C₁-C₈ alkyl;
C₃-C₆ cycloalkyl;
phenyl unsubstituted or substituted with at least one group selected from a —O—C₁-C₄-alkyl and C₁-C₄-alkyl;
benzothiophene;
a 5 or 6 membered-heteroaromatic ring;
R³ is selected from the group consisting of:
C₁-C₈ alkyl;
(CH₂)ₘCOCH₃, wherein m is an integer comprised between 1 and 4;
(C₂)ₙ—Z, wherein n is an integer comprised between 1 and 3 and Z is selected from the group consisting of dialkylamine, C₃-C₆-cycloalkyl, benzotriazole, isoindol-1,3(2H)-dione-2-yl, imidazole, triazole, indole, furane, and phenyl, the latter being unsubstituted or substituted with one or more groups selected from halo, C₁-C₃ alkyl, O—C₁-C₃ alkyl and C₁-C₃ alkylamino;
-C₃-C₆ cycloalkyl unsubstituted or substituted with one or more groups selected from halo, and C₁-C₃ alkyl;
2-methyl-1,3-oxazol-4-yl;
phenyl unsubstituted or substituted with one or more groups selected from C₁-C₃ alkyl, hydroxyl, halo and nitro.

2. A method claimed in claim 1 wherein X is O and Y is NH.

3. A method claimed in claim 1 wherein R¹ is selected from methyl, cyclopropyl and trifluoromethyl.

4. A method claimed in claim 1, wherein R² is selected from methoxyphenyl, methylphenyl, 1-benzothiophen-3-yl, 1-ethylpropyl, 1-methyl-1H-pyrrol-2-yl, 2-methylethyl, pyridin-3yl, cyclopentyl and cyclohexyl.

5. A method claimed in claim 1, wherein R³ is selected from: C₂-C₄ alkyl; 4yl-butan-2one; —CH₂—Z wherein Z is dimethylamino, cyclopentyl, benzotriazol-1-yl, isoindol 1,3 (2H)-dione-2-yl, imidazol-4-yl, 1,2,3-triazol-1-yl, indol-1-yl, furan-2-yl, or phenyl, unsubstituted or substituted with one or more groups selected from F, methyl, methoxy and dimethylamino; C₃-C₆ cycloalkyl unsubstituted or substituted with one or more groups selected from F and methyl; 2-methyl-1,3-oxazol-4-yl; phenyl unsubstituted or substituted with one or more groups selected from methyl, hydroxy, F and nitro; dimethylamino.

6. A method claimed in claim 1, wherein R³ is selected from 1-methylen-1H-benzotriazol, 2-methyl-1,3-oxazol-4-yl, 2-methylen-1H-isoindole-1,3(2H)-dione, N,N-dimethyl-1-methylenamine, 4-methylen-1H-imidazole, 4-yl-butan-2-one, 1-methylen-1H-1,2,3-triazol; 1-methylen-1H-indole, benzyl, 2-methoxybenzyl, 2-methylbenzyl, 3-methylbenzyl, 4-methylbenzyl, 2,3-difluorobenzyl, 4-fluorobenzyl, 2,6-difluorobenzyl, 4-N,N-dimethylaminobenzyl, 4-methylphenyl, 4-hydroxyphenyl, 4-nitrophenyl, 2-nitrophenyl, 4-fluorophenyl, 2-methylenfurane, ethyl, butyl, isobutyl, phenyl, 4,4-difluorocyclohexyl, cyclohexyl, cyclopentyl, cyclobutyl, cyclopropyl, 1-yl-2-methylcyclopropane, methylencyclopentyl.

7. A method claimed in claim 1, wherein said compound of formula (I) is selected from:
2-(1H-benzotriazol-1-yl)-N-(2-methoxybenzyl)-N-{1-(4-methylphenyl)-2-oxo-2-[(tetrahydrofuran-2-ylmethyl)amino]ethyl}acetamide;
2-methyl-N-(2-methoxybenzyl)-N-{1-(4-methylphenyl)-2-oxo-2-[(tetrahydrofuran-2-ylmethyl)amino]ethyl}-1,3-oxazole-4-carboxamide;
2-(2,3-difluorophenyl)-N-(2-methoxybenzyl)-N-{1-(4-methylphenyl)-2-oxo-2-[(tetrahydrofuran-2-ylmethyl)amino]ethyl}acetamide;
N-(2-methoxybenzyl)-N-{1-(4-methylphenyl)-2-oxo-2-[(tetrahydrofuran-2-ylmethyl)amino]ethyl}furan-2-carboxamide;
2-(2,4-difluorophenyl)-N-(2-methoxybenzyl)-N-{1-(4-methylphenyl)-2-oxo-2-[(tetrahydrofuran-2-ylmethyl)amino]ethyl}acetamide;
2-(2,6-difluorophenyl)-N-(2-methoxybenzyl)-N-{1-(4-methylphenyl)-2-oxo-2-[(tetrahydrofuran-2-ylmethyl)amino]ethyl}acetamide;
N-(2-methoxybenzyl)-N-{1-(4-methylphenyl)-2-oxo-2-[(tetrahydrofuran-2-ylmethyl)amino]ethyl}-2-phenylacetamide;
3-methyl-N-(2-methoxybenzyl)-N-{(1-(4-methylphenyl)-2-oxo-2-[(tetrahydrofuran-2-ylmethyl)amino]ethyl}butanamide;
2-(2-methylphenyl)-N-(2-methoxybenzyl)-N-{(1-(4-methylphenyl)-2-oxo-2-[(tetrahydrofuran-2-ylmethyl)amino]ethyl}acetamide;
2-(1,3-dioxoisoindolin-2-yl)-N-(2-methoxybenzyl)-N-{1-(4-methylphenyl)-2-oxo-2-[(tetrahydrofuran-2-ylmethyl)amino]-ethyl}acetamide;
2-(dimethylamino)-N-(2-methoxybenzyl)-{1-(4-methylphenyl)-2-oxo-2-[(tetrahydrofuran-2-ylmethyl)amino]ethyl}acetamide;
2-(1H-imidazol-4-yl)-N-(2-methoxybenzyl)-N-{1-(4-methylphenyl)-2-oxo-2-[(tetrahydrofuran-2-ylmethyl)amino]ethyl}acetamide;
2-(2-methoxyphenyl)-N-(2-methoxybenzyl)-N-{(1-(4-methylphenyl)-2-oxo-2-[(tetrahydrofuran-2-ylmethyl)amino]ethyl}acetamide;
N-(2-methoxybenzyl)-N-{1-(4-methylphenyl)-2-oxo-2-[(tetrahydrofuran-2-ylmethyl)amino]ethyl}pentanamide;
N-(2-methoxybenzyl)-N-{1-(4-methylphenyl)-2-oxo-2-[(tetrahydrofuran-2-ylmethyl)amino]ethyl}cyclopentanecarboxamide;
4-hydroxy-N-(2-methoxybenzyl)-N-{1-(4-methylphenyl)-2-oxo-2-[(tetrahydrofuran-2-ylmethyl)amino]ethyl}benzamide;
4-oxo-N-(2-methoxybenzyl)-N-{1-(4-methylphenyl)-2-oxo-2-[(tetrahydrofuran-2-ylmethyl)amino]ethyl}pentanamide;
2-(3-methylphenyl)-N-(2-methoxybenzyl)-N-{(1-(4-methylphenyl)-2-oxo-2-[(tetrahydrofuran-2-ylmethyl)amino]ethyl}acetamide;
2-(4-methylphenyl)-N-(2-methoxybenzyl)-N-{(1-(4-methylphenyl)-2-oxo-2-[(tetrahydrofuran-2-ylmethyl)amino]ethyl}acetamide;
4-methyl-N-(2-methoxybenzyl)-N-{1-(4-methylphenyl)-2-oxo-2-[(tetrahydrofuran-2-ylmethyl)amino]ethyl}benzamide;
2-(4-fluorophenyl)-N-(2-methoxybenzyl)-N-{(1-(4-methylphenyl)-2-oxo-2-[(tetrahydrofuran-2-ylmethyl)amino]ethyl}acetamide;
4-fluoro-N-(2-methoxybenzyl)-N-{1-(4-methylphenyl)-2-oxo-2-[(tetrahydrofuran-2-ylmethyl)amino]ethyl}benzamide;
4,4-difluoro-N-(2-methoxybenzyl)-N-{1-(4-methylphenyl)-2-oxo-2-[(tetrahydrofuran-2-ylmethyl)amino]ethyl}cyclohexanecarboxamide;
N-(2-methoxybenzyl)-N-{1-(4-methylphenyl)-2-oxo-2-[(tetrahydrofuran-2-ylmethyl)amino]ethyl}propanamide;

N-(2-methoxybenzyl)-N-{1-(4-methylphenyl)-2-oxo-2-[(tetrahydrofuran-2-ylmethyl)amino]ethyl}cyclobutanecarboxamide;
N-(2-methoxybenzyl)-2-nitro-N-{1-(4-methylphenyl)-2-oxo-2-[(tetrahydrofuran-2-ylmethyl)amino]ethyl}benzamide;
N-(2-methoxybenzyl)-N-{1-(4-methylphenyl)-2-oxo-2-[(tetrahydrofuran-2-ylmethyl)amino]ethyl}cyclopropanecarboxamide;
N-(2-methoxybenzyl)-4-nitro-N-{1-(4-methylphenyl)-2-oxo-2-[(tetrahydrofuran-2-ylmethyl)amino]ethyl}benzamide;
2-[(4-dimethylamino)phenyl]-N-(2-methoxybenzyl)-N-{1-(4-methylphenyl)-2-oxo-2-[(tetrahydrofuran-2-ylmethyl)amino]ethyl}acetamide;
N-(2-methoxybenzyl)-N-{1-(4-methylphenyl)-2-oxo-2-[(tetrahydrofuran-2-ylmethyl)amino]ethyl}-2-(1H-1,2,3-triazol-1-yl)acetamide;
2-(1H-indol-1-yl)-N-(2-methoxybenzyl)-N-{1-(4-methylphenyl)-2-oxo-2-[(tetrahydrofuran-2-ylmethyl)amino]ethyl}acetamide;
N-(cyclopentylmethyl)-2-(1H-imidazol-4-yl)-N-{1-(4-methylphenyl)-2-oxo-2-[(tetrahydrofuran-2-ylmethyl)amino]ethyl}acetamide;
N-(cyclohexylmethyl)-2-(2-methylphenyl)-N-{1-(4-methylphenyl)-2-oxo-2-[(tetrahydrofuran-2-ylmethyl)amino]ethyl}acetamide;
N-(cyclohexylamino)-2-(dimethylamino)-N-{1-(4-methylphenyl)-2-oxo-2-[(tetrahydrofuran-2-ylmethyl)amino]ethyl}acetamide;
2-(dimethylamino)-N-(3-methylbenzyl)-N-{1-(4-methylphenyl)-2-oxo-2-[(tetrahydrofuran-2-ylmethyl)amino]ethyl}acetamide;
N-(cyclohexylmethyl)-2-(1H-imidazol-4-yl)-N-{1-(4-methylphenyl)-2-oxo-2-[(tetrahydrofuran-2-ylmethyl)amino]ethyl}acetamide;
N-(cyclohexylmethyl)-2-phenyl-N-{1-(4-methylphenyl)-2-oxo-2-[(tetrahydrofuran-2-ylmethyl)amino]ethyl}acetamide;
2-methyl-N-(3-methylbenzyl)-N-{1-(4-methylphenyl)-2-oxo-2-[(tetrahydrofuran-2-ylmethyl)amino]ethyl}cyclopropanecarboxamide;
N-(1-benzothiophen-3-ylmethyl)-2-(dimethylamino)-N-{1-(4-methylphenyl)-2-oxo-2-[(tetrahydrofuran-2-ylmethyl)amino]ethyl}acetamide;
N-(cyclohexylmethyl)-2-(3-methylphenyl)-N-{1-(4-methylphenyl)-2-oxo-2-[(tetrahydrofuran-2-ylmethyl)amino]ethyl}acetamide;
N-(2-ethylbutyl)-2-(2-methylphenyl)-N-{1-(4-methylphenyl)-2-oxo-2-[(tetrahydrofuran-2-ylmethyl)amino]ethyl}acetamide;
N-(2-ethylbutyl)-2-(4-fluorolphenyl)-N-{1-(4-methylphenyl)-2-oxo-2-[(tetrahydrofuran-2-ylmethyl)amino]ethyl}acetamide;
2-(dimethylamino)-N-[(1-methyl-1H-pyrrol-2-yl)methyl]-N-{1-(4-methylphenyl)-2-oxo-2-[(tetrahydrofuran-2-ylmethyl)amino]ethyl}acetamide;
N-(cyclopentylmethyl)-2-(2-methylphenyl)-N-{1-(4-methylphenyl)-2-oxo-2-[(tetrahydrofuran-2-ylmethyl)amino]ethyl}acetamide;
N-(cyclopentylmethyl)-2-(3-methylphenyl)-N-{1-(4-methylphenyl)-2-oxo-2-[(tetrahydrofuran-2-ylmethyl)amino]ethyl}acetamide;
2-(2-methylphenyl)-N-(pyridin-3-ylmethyl)-N-{1-(4-methylphenyl)-2-oxo-2-[(tetrahydrofuran-2-ylmethyl)amino]ethyl}acetamide;
N-(cyclopentylmethyl)-N-{1-(4-methylphenyl)-2-oxo-2-[(tetrahydrofuran-2-yl)methylamino]ethyl}2-phenylacetamide;
N-(cyclohexylmethyl)-2-cyclopentyl-N-{1-(4-methylphenyl)-2-oxo-2-[(tetrahydrofuran-2-ylmethyl)amino]ethyl}acetamide;
2-(1H-imidazol-4-yl)-N-(2-methylpropyl)-N-{1-(4-methylphenyl)-2-oxo-2-[(tetrahydrofuran-2-ylmethyl)amino]ethyl}acetamide;
N-(2-ethylbutyl)-N-{1-(4-methylphenyl)-2-oxo-2-[(tetrahydrofuran-2-ylmethyl)amino]ethyl}cyclohexanecarboxamide;
2-cyclopentyl-N-cyclopentylmethyl-N-{1-(4-methylphenyl)-2-oxo-2-[(tetrahydrofuran-2-ylmethyl)amino]ethyl}acetamide;
N-(2-methoxybenzyl)-N-[1-(4-cyclopropylphenyl)-2-oxo-2-[(tetrahydrofuran-2-yl)methylamino]ethyl)-3-methylbutanamide;
2-(1H-benzotriazol-1-yl)-N-(2-methoxybenzyl)-N-{1-(4-trifluoromethylphenyl)-2-oxo-2-[(tetrahydrofuran-2-ylmethyl)amino]ethyl}acetamide;
N-[(2-methoxybenzyl)-N-{1-[4-(trifluoromethyl)phenyl]-2-oxo-2-[(tetrahydrofuran-2-yl)methylamino]ethyl}3-methylbutanamide;
N-(2-methoxybenzyl)-N-{(1R)-1-(4-methylphenyl)-2-oxo-2-[(2R)-(pyrrolidin-2-ylmethyl)amino]ethyl}-2-(1H-1,2,3-triazol-1-yl)acetate.

8. A method claimed in claim 1, wherein said compound of formula (I) is in the R,R configuration.

9. A method claimed in claim 1, wherein said compound of formula (I) is as a mixture of stereoisomers.

10. A method as claimed in claim 1, wherein said pain-related disorder or disease is selected from visceral pain, neuropathic pain, post herpetic neuralgia, nerve injury, central pain syndromes caused by a lesion of the nervous system, postsurgical pain syndromes, bone and joint pain, repetitive motion pain, dental pain, cancer pain, myofascial pain, fibromyalgia, perioperative pain, chronic pain, dysmenorrhea, pain associated with angina and inflammatory pain.

11. A method as claimed in claim 1, wherein said pain-related disorder or disease is pain associated with osteoarthritis, rheumatoid arthritis, rheumatic disease, gout, hyper-reactive airways and airways disease.

12. A method as claimed in claim 1, wherein said pain-related disorder or disease is pain is associated with pancreatitis, cystitis or renal colic.

13. A compound of formula (I):

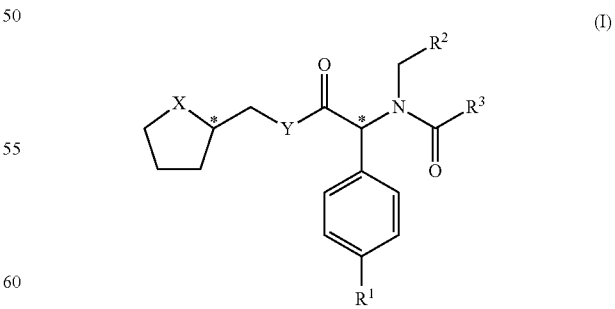

or a pharmaceutically acceptable salt thereof, wherein
X and Y are different one from the other and are O or NH;
$R^1$ is selected from the group consisting of
$C_1$-$C_6$-alkyl; $C_3$-$C_6$-cycloalkyl and halo $C_1$-$C_3$-alkyl;
$R^2$ is selected from the group consisting of:

C₁-C₈ alkyl;
C₃-C₆ cycloalkyl;
phenyl unsubstituted or substituted with at least one group selected from a —O—C₁-C₄-akyl and C₁-C₄-alkyl;
benzothiophene;
a 5 or 6 membered-heteroaromatic ring;
R³ is selected from the group consisting of:
C₁-C₈ alkyl;
(CH₂)ₘCOCH₃, wherein m is an integer comprised between 1 and 4;
(CH₂)ₙ—Z, wherein n is an integer comprised between 1 and 3 and Z is selected from the group consisting of dialkylamine, C₃-C₆-cycloalkyl, isoindol-1,3(2H)-dione-2-yl, imidazole, triazole, indole, furane, and phenyl, the latter being unsubstituted or substituted with one or more groups selected from halo, C₁-C₃ alkyl, O—C₁-C₃ alkyl and C₁-C₃ alkylamino; —C₃-C₆ cycloalkyl unsubstituted or substituted with one or more groups selected from halo, and C₁-C₃ alkyl;
2-methyl-1,3-oxazol-4-yl;
phenyl unsubstituted or substituted with one or more groups selected from C₁-C₃ alkyl, hydroxyl, halo and nitro.

14. A compound as claimed in claim 13, wherein X is O and Y is NH.

15. A compound as claimed in claim 13, wherein R¹ is selected from methyl, cyclopropyl and trifluoromethyl.

16. A compound as claimed in claim 13, wherein R² is selected from methoxyphenyl, methylphenyl, 1-benzothiophen-3-yl, 1-ethylpropyl, 1-methyl-1H-pyrrol-2-yl, 2-methylethyl, pyridin-3yl, cyclopentyl and cyclohexyl.

17. A compound as claimed in in claim 12, wherein R³ is selected from: C₂-C₄ alkyl; 4-yl-butan-2one; —CH₂—Z wherein Z is dimethylamino, cyclopentyl, -1-yl, isoindol-1,3 (2H)-dione-2-yl, imidazol-4-yl, 1,2,3-triazol-1-yl, indol-1-yl, furan-2-yl, or phenyl, unsubstituted or substituted with one or more groups selected from F, methyl, methoxy and dimethylamino; C₃-C₆ cycloalkyl unsubstituted or substituted with one or more groups selected from F and methyl; 2-methyl-1,3-oxazol-4-yl; phenyl unsubstituted or substituted with one or more groups selected from methyl, hydroxy, F and nitro; dimethylamino.

18. A compound as claimed in claim 13, wherein R³ is selected from 2-methyl-1,3-oxazol-4-yl, 2-methylen-1H-isoindole-1,3(2H)-dione, N,N-dimethyl-1-methylenamine, 4-methylen-1H-imidazole, 4-yl-butan-2-one, 1-methylen-1H-1,2,3-triazole; 1-methylen-1H-indole, benzyl, 2-methoxybenzyl, 2-methylbenzyl, 3-methylbenzyl, 4-methylbenzyl, 2,3-difluorobenzyl, 4-fluorobenzyl, 2,6-difluorobenzyl, 4-N,N-dimethylaminobenzyl, 4-methylphenyl, 4-hydroxyphenyl, 4-nitrophenyl, 2-nitrophenyl, 4-fluorophenyl, 2-methylenfurane, ethyl, butyl, isobutyl, phenyl, 4,4-difluorocyclohexyl, cyclohexyl, cyclopentyl, cyclobutyl, cyclopropyl, 1-yl-2-methylcyclopropane, methylencyclopentyl.

19. A compound as claimed in claim 13, selected from:
2-methyl-N-(2-methoxybenzyl)-N-{1-(4-methylphenyl)-2-oxo-2-[(tetrahydrofuran-2-ylmethyl)amino]ethyl}-1,3-oxazole-4-carboxamide;
2-(2,3-difluorophenyl)-N-(2-methoxybenzyl)-N-{1-(4-methylphenyl)-2-oxo-2-[(tetrahydrofuran-2-ylmethyl) amino]ethyl}acetamide;
N-(2-methoxybenzyl)-N-{1-(4-methylphenyl)-2-oxo-2-[(tetrahydrofuran-2-ylmethyl)amino]ethyl}furan-2-carboxamide;
2-(2,4-difluorophenyl)-N-(2-methoxybenzyl)-N-{1-(4-methylphenyl)-2-oxo-2-[(tetrahydrofuran-2-ylmethyl) amino]ethyl}acetamide;
2-(2,6-difluorophenyl)-N-(2-methoxybenzyl)-N-{1-(4-methylphenyl)-2-oxo-2-[(tetrahydrofuran-2-ylmethyl) amino]acetamide;
N-(2-methoxybenzyl)-N-{1-(4-methylphenyl)-2-oxo-2-[(tetrahydrofuran-2-ylmethyl)amino]ethyl}-2-phenylacetamide;
3-methyl-N-(2-methoxybenzyl)-N-{(1-(4-methylphenyl)-2-oxo-2-[(tetrahydrofuran-2-ylmethyl)amino] ethyl}butanamide;
2-(2-methylphenyl)-N-(2-methoxybenzyl)-N-{(1-(4-methylphenyl)-2-oxo-2-[(tetrahydrofuran-2-ylmethyl) amino]ethyl}acetamide;
2-(1,3-dioxoisoindolin-2-yl)-N-(2-methoxybenzyl)-N-{1-(4-methylphenyl)-2-oxo-2-[(tetrahydrofuran-2-ylmethyl)amino]-ethyl}acetamide;
2-(dimethylamino)-N-(2-methoxybenzyl)-{1-(4-methylphenyl)-2-oxo-2-[(tetrahydrofuran-2-ylmethyl) amino]ethyl}acetamide;
2-(1H-imidazol-4-yl)-N-(2-methoxybenzyl)-N-{(1-(4-methylphenyl)-2-oxo-2-[(tetrahydrofuran-2-ylmethyl) amino]ethyl}acetamide;
2-(2-methoxyphenyl)-N-(2-methoxybenzyl)-N-{(1-(4-methylphenyl)-2-oxo-2-[(tetrahydrofuran-2-ylmethyl) amino]ethyl}acetamide;
N-(2-methoxybenzyl)-N-{1-(4-methylphenyl)-2-oxo-2-[(tetrahydrofuran-2-ylmethyl)amino] ethyl}pentanamide;
N-(2-methoxybenzyl)-N-{1-(4-methylphenyl)-2-oxo-2-[(tetrahydrofuran-2-ylmethyl)amino] ethyl}cyclopentanecarboxamide;
4-hydroxy-N-(2-methoxybenzyl)-N-{1-(4-methylphenyl)-2-oxo-2-[(tetrahydrofuran-2-ylmethyl)amino] ethyl}benzamide;
4-oxo-N-(2-methoxybenzyl)-N-{1-(4-methylphenyl)-2-oxo-2-[(tetrahydrofuran-2-ylmethyl)amino] ethyl}pentanamide;
2-(3-methylphenyl)-N-(2-methoxybenzyl)-N-{(1-(4-methylphenyl)-2-oxo-2-[(tetrahydrofuran-2-ylmethyl) amino]ethyl}acetamide;
2-(4-methylphenyl)-N-(2-methoxybenzyl)-N-{(1-(4-methylphenyl)-2-oxo-2-[(tetrahydrofuran-2-ylmethyl) amino]ethyl}acetamide;
4-methyl-N-(2-methoxybenzyl)-N-{1-(4-methylphenyl)-2-oxo-2-[(tetrahydrofuran-2-ylmethyl)amino] ethyl}benzamide;
2-(4-fluorophenyl)-N-(2-methoxybenzyl)-N-{(1-(4-methylphenyl)-2-oxo-2-[(tetrahydrofuran-2-ylmethyl) amino]ethyl}acetamide;
4-fluoro-N-(2-methoxybenzyl)-N-{1-(4-methylphenyl)-2-oxo-2-[(tetrahydrofuran-2-ylmethyl)amino] ethyl}benzamide;
4,4-difluoro-N-(2-methoxybenzyl)-N-{1-(4-methylphenyl)-2-oxo-2-[(tetrahydrofuran-2-ylmethyl)amino] ethyl}cyclohexanecarboxamide;
N-(2-methoxybenzyl)-N-{1-(4-methylphenyl)-2-oxo-2-[(tetrahydrofuran-2-ylmethyl)amino] ethyl}propanamide;
N-(2-methoxybenzyl)-N-{1-(4-methylphenyl)-2-oxo-2-[(tetrahydrofuran-2-ylmethyl)amino] ethyl}cyclobutanecarboxamide;
N-(2-methoxybenzyl)-2-nitro-N-{1-(4-methylphenyl)-2-oxo-2-[(tetrahydrofuran-2-ylmethyl)amino] ethyl}benzamide;
N-(2-methoxybenzyl)-N-{1-(4-methylphenyl)-2-oxo-2-[(tetrahydrofuran-2-ylmethyl)amino] ethyl}cyclopropanecarboxamide;

N-(2-methoxybenzyl)-4-nitro-N-{1-(4-methylphenyl)-2-oxo-2-[(tetrahydrofuran-2-ylmethyl)amino]ethyl}benzamide;
2-[(4-dimethylamino)phenyl]-N-(2-methoxybenzyl)-N-{1-(4-methylphenyl)-2-oxo-2-[(tetrahydrofuran-2-ylmethyl)amino]ethyl}acetamide;
N-(2-methoxybenzyl)-N-{1-(4-methylphenyl)-2-oxo-2-[(tetrahydrofuran-2-ylmethyl)amino]ethyl}-2-(1H-1,2,3-triazol-1-yl)acetamide;
2-(1H-indol-1-yl)-N-(2-methoxybenzyl)-N-{1-(4-methylphenyl)-2-oxo-2-[(tetrahydrofuran-2-ylmethyl)amino]ethyl}acetamide;
N-(cyclopentylmethyl)-2-(1H-imidazol-4-yl)-N-{1-(4-methylphenyl)-2-oxo-2-[(tetrahydrofuran-2-ylmethyl)amino]ethyl}acetamide;
N-(cyclohexylmethyl)-2-(2-methylphenyl)-N-{1-(4-methylphenyl)-2-oxo-2-[(tetrahydrofuran-2-ylmethyl)amino]ethyl}acetamide;
N-(cyclohexylamino)-2-(dimethylamino)-N-{1-(4-methylphenyl)-2-oxo-2-[(tetrahydrofuran-2-ylmethyl)amino]ethyl}acetamide;
2-(dimethylamino)-N-(3-methylbenzyl)-N-{1-(4-methylphenyl)-2-oxo-2-[(tetrahydrofuran-2-ylmethyl)amino]ethyl}acetamide;
N-(cyclohexylmethyl)-2-(1H-imidazol-4-yl)-N-{1-(4-methylphenyl)-2-oxo-2-[(tetrahydrofuran-2-ylmethyl)amino]ethyl}acetamide;
N-(cyclohexylmethyl)-2-phenyl-N-{1-(4-methylphenyl)-2-oxo-2-[(tetrahydrofuran-2-ylmethyl)amino]ethyl}acetamide;
2-methyl-N-(3-methylbenzyl)-N-{1-(4-methylphenyl)-2-oxo-2-[(tetrahydrofuran-2-ylmethyl)amino]ethyl}cyclopropanecarboxamide;
N-(1-benzothiophen-3-ylmethyl)-2-(dimethylamino)-N-{1-(4-methylphenyl)-2-oxo-2-[(tetrahydrofuran-2-ylmethyl)amino]ethyl}acetamide;
N-(cyclohexylmethyl)-2-(3-methylphenyl)-N-{1-(4-methylphenyl)-2-oxo-2-[(tetrahydrofuran-2-ylmethyl)amino]ethyl}acetamide;
N-(2-ethylbutyl)-2-(2-methylphenyl)-N-{1-(4-methylphenyl)-2-oxo-2-[(tetrahydrofuran-2-ylmethyl)amino]ethyl}acetamide;
N-(2-ethylbutyl)-2-(4-fluorolphenyl)-N-{1-(4-methylphenyl)-2-oxo-2-[(tetrahydrofuran-2-ylmethyl)amino]ethyl}acetamide;
2-(dimethylamino)-N-[(1-methyl-1H-pyrrol-2-yl)methyl]-N-{1-(4-methylphenyl)-2-oxo-2-[(tetrahydrofuran-2-ylmethyl)amino]ethyl}acetamide;
N-(cyclopentylmethyl)-2-(2-methylphenyl)-N-{1-(4-methylphenyl)-2-oxo-2-[(tetrahydrofuran-2-ylmethyl)amino]ethyl}acetamide;
N-(cyclopentylmethyl)-2-(3-methylphenyl)-N-{1-(4-methylphenyl)-2-oxo-2-[(tetrahydrofuran-2-ylmethyl)amino]ethyl}acetamide;
2-(2-methylphenyl)-N-(pyridin-3-ylmethyl)-N-{1-(4-methylphenyl)-2-oxo-2-[(tetrahydrofuran-2-ylmethyl)amino]ethyl}acetamide;
N-(cyclopentylmethyl)-N-{1-(4-methylphenyl)-2-oxo-2-[(tetrahydrofuran-2-yl)methylamino]ethyl}2-phenylacetamide;
N-(cyclohexylmethyl)-2-cyclopentyl-N-{1-(4-methylphenyl)-2-oxo-2-[(tetrahydrofuran-2-ylmethyl)amino]ethyl}acetamide;
2-(1H-imidazol-4-yl)-N-(2-methylpropyl)-N-{1-(4-methylphenyl)-2-oxo-2-[(tetrahydrofuran-2-ylmethyl)amino]ethyl}acetamide;
N-(2-ethylbutyl)-N-{1-(4-methylphenyl)-2-oxo-2-[(tetrahydrofuran-2-ylmethyl)amino]ethyl}cyclohexanecarboxamide;
2-cyclopentyl-N-cyclopentylmethyl-N-{1-(4-methylphenyl)-2-oxo-2-[(tetrahydrofuran-2-ylmethyl)amino]ethyl}acetamide;
N-(2-methoxybenzyl]-N-[1-(4-cyclopropylphenyl)-2-oxo-2-[(tetrahydrofuran-2-yl)methylamino]ethyl)-3-methylbutanamide;
N-[(2-methoxybenzyl]-N-{1-[4-(trifluoromethyl)phenyl]-2-oxo-2-[(tetrahydrofuran-2-yl)methylamino]ethyl}3-methylbutanamide;
N-(2-methoxybenzyl)-N-{(1R)-1-(4-methylphenyl)-2-oxo-2-[(2R)-(pyrrolidin-2-ylmethyl)amino]ethyl}-2-(1H-1,2,3-triazol-1-yl)acetate.

20. A compound as claimed in claim 13, in the R,R configuration.

21. A compound as claimed in claim 13, as a mixture of stereoisomers.

22. A pharmaceutical composition comprising at least one compound as claimed in claim 13 in combination with pharmaceutically acceptable excipients and/or diluents.

* * * * *